United States Patent
Boyanov et al.

(10) Patent No.: US 10,545,115 B2
(45) Date of Patent: Jan. 28, 2020

(54) BIOCHEMICALLY ACTIVATED ELECTRONIC DEVICE

(71) Applicant: ILLUMINA, INC., San Diego, CA (US)

(72) Inventors: Boyan Boyanov, San Diego, CA (US); Jeffrey G. Mandell, San Diego, CA (US); Jingwei Bai, San Diego, CA (US); Kevin L. Gunderson, Encinitas, CA (US); Cheng-Yao Chen, Eugene, OR (US); Michel Perbost, Woburn, MA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/839,795

(22) Filed: Dec. 12, 2017

(65) Prior Publication Data

US 2018/0112265 A1 Apr. 26, 2018

Related U.S. Application Data

(63) Continuation of application No. 14/798,762, filed on Jul. 14, 2015.

(60) Provisional application No. 62/171,523, filed on Jun. 5, 2015, provisional application No. 62/161,709, filed on May 14, 2015, provisional application No. 62/069,198, filed on Oct. 27, 2014, provisional application No. 62/024,856, filed on Jul. 15, 2014.

(51) Int. Cl.
| | | |
|---|---|---|
| C12N 9/00 | (2006.01) | |
| C12N 9/96 | (2006.01) | |
| G01N 27/414 | (2006.01) | |
| C12Q 1/6869 | (2018.01) | |

(52) U.S. Cl.
CPC ....... *G01N 27/4145* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 5,599,675 A | 2/1997 | Brenner | |
| 5,750,341 A | 5/1998 | Macevicz | |
| 5,968,784 A * | 10/1999 | Spinella | C12N 15/1096 435/6.11 |
| 6,355,431 B1 | 3/2002 | Chee et al. | |
| 6,890,741 B2 | 5/2005 | Fan et al. | |
| 6,908,763 B1 | 6/2005 | Akashi et al. | |
| 6,913,884 B2 | 7/2005 | Stuelpnagel et al. | |
| 7,057,026 B2 | 6/2006 | Barnes et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,414,116 B2 | 8/2008 | Milton et al. | |
| 7,427,673 B2 | 9/2008 | Balasubramanian et al. | |
| 7,556,922 B2 | 7/2009 | Block et al. | |
| 7,582,420 B2 | 9/2009 | Oliphant et al. | |
| 7,923,731 B2 * | 4/2011 | Jiang | B82Y 10/00 257/66 |
| 2005/0053980 A1 | 3/2005 | Gunderson et al. | |
| 2005/0181440 A1 | 8/2005 | Chee et al. | |
| 2007/0099208 A1 | 5/2007 | Drmanac et al. | |
| 2008/0108082 A1 | 5/2008 | Rank et al. | |
| 2009/0032401 A1 | 2/2009 | Ronaghi et al. | |
| 2009/0186349 A1 | 7/2009 | Gunderson et al. | |
| 2010/0073847 A1 | 3/2010 | Martin | |
| 2010/0111768 A1 | 5/2010 | Banerjee et al. | |
| 2011/0312529 A1 | 12/2011 | He et al. | |
| 2013/0078622 A1 | 3/2013 | Collins et al. | |
| 2013/0165328 A1 | 6/2013 | Previte et al. | |
| 2013/0240359 A1 | 9/2013 | Turner et al. | |
| 2014/0186547 A1 * | 7/2014 | Wu | B01J 15/005 427/545 |
| 2015/0065353 A1 | 3/2015 | Turner et al. | |

FOREIGN PATENT DOCUMENTS

| | | |
|---|---|---|
| JP | 2010513869 | 4/2010 |
| WO | 8910977 | 11/1989 |
| WO | 1991/006678 | 5/1991 |
| WO | 0125480 | 4/2001 |
| WO | 2004/018497 | 3/2004 |
| WO | 2007/123744 | 11/2007 |
| WO | 2008/076406 | 6/2008 |
| WO | 2008/107014 | 9/2008 |
| WO | 2010/068884 | 6/2010 |
| WO | 2012/116191 | 8/2012 |

(Continued)

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Archaea," Wikipedia.com (accessed May 11, 2016).*
"Algae," Wikipedia.com (accessed Mar. 4, 2016).*
"Protozoa," Wikipedia.com (accessed May 11, 2016).*

(Continued)

*Primary Examiner* — Bradley L. Sisson

(74) *Attorney, Agent, or Firm* — Illumina, Inc.

(57) ABSTRACT

A method of nucleic acid sequencing. The method can include the steps of (a) providing a polymerase tethered to a solid support charge sensor; (b) providing one or more nucleotides, whereby the presence of the nucleotide can be detected by the charge sensor; and (c) detecting incorporation of the nucleotide into a nascent strand complementary to a template nucleic acid.

28 Claims, 12 Drawing Sheets

(56) References Cited

FOREIGN PATENT DOCUMENTS

| WO | 2013/056241 | 4/2013 |
|---|---|---|
| WO | 2013/154999 | 10/2013 |

OTHER PUBLICATIONS

"List of sequenced bacterial genomes" (Wikipedia.com; accessed Jan. 24, 2014).*

"Custom Antibody Services," Precision Antibodies, accessed Apr. 16, 2014.*

Bentley, et al., "Accurate whole human genome sequencing using reversible terminator chemistry", Nature, vol. 456, Nov. 6, 2008, 53-59.

Besteman, "Enzyme-Coated Carbon Nanotubes as Single-Molecule Biosensors", Nano Letters; vol. 3. No. 6, 727-730.

Briseno, et al., "Introducing organic nanowire transistors", Materials Today; vol. 11 No. 4, Apr. 2008, 38-47.

Chen, "Noncovalent functionalization of carbon nanotubes for highly specific electronic biosensors", PNAS; vol. 100; No. 9, Apr. 29, 2003, 4984-4989.

Chen, et al., "Noncovalent Sidewall Functionalization of Single-Walled Carbon Nanotubes for Protein Immobilization", J. Am. Chem. Soc.; vol. 123, No. 16, 2001, 3838-3839.

Choi, et al., "Dissecting Single-Molecule Signal Transduction in Carbon Nanotube Circuits with Protein Engineering", Nano Letters, 2013, 625-631.

Choi, et al., "Single-Molecule Lysozyme Dynamics Monitored by an Electronic Circuit", Science; vol. 335, Jan. 20, 2012, 319-324.

Cui, et al., "High Performance Silicon Nanowire Field Effect Transistors", Nano Letters; vol. 3, No. 2, 2003, 149-152.

Fleissner, "Site-directed spin labeling of a genetically encoded unnatural amino acid", PNAS; vol. 106; No. 51, Dec. 22, 2009, 21637-21642.

Goldsmith, "Conductance-Controlled Point Functionalization of Single-Walled Carbon Nanotubes", Science; vol. 315, Jan. 5, 2007, 77-81.

Gruner, "Carbon nanotube transistors for biosensing applications", Anal. Bioanal Chem; vol. 384, 2006, 322-335.

Huang, et al., "Sub 50-nm FinFET: PMOS", IEDM, 1999, 67-70.

Ionescu, "Tunnel field-effect transistors as energy-efficient electronic switches", Nature; vol. 479, Nov. 17, 2011, 329-337.

Lamichhane, et al., "Dynamics of Site Switching in DNA Polymerase", J. Am. Chem. Soc. vol. 135, 2013, 4735-4742.

MacDiarmid, "Synthetic Metals: A Novel Role for Organic Polymers (Nobel Lecture)", Angew. Chem. Int. Ed. vol. 40, 2001, 2581-2590.

McNeill, et al., "Electronic Conduction in Polymers—I. The Chemical Structure of Polypyrrole", Aust. J. Chem. vol. 16, 1963, 1056-1075.

Nishiguchi, et al., "Single-Electron Stochastic Resonance Using Si Nanowire Transistors", Japanese Journal of Applied Physics; vol. 50, 2011.

Olsen, et al., "Electronic Measurements of Single-Molecule Processing by DNA Polymerase I (Klenow Fragment)", J Am Chem Soc 135(21), May 2013, pp. 7855-7860.

Sarkar, "Proposal for tunnel-field-effect-transistor as ultra-sensitive and label-free biosensors", Appl. Phys. Lett. vol. 100, 2012.

Star, et al., "Electronic Detection of Specific Protein Binding Using Nanotube FET Devices", Nano Letters; vol. 3; No. 4, 2003, 459-463.

Star, et al., "Electronic Detection of the Enzymatic Degradation of Starch", Organic Letters; vol. 6; No. 13, 2004, 2089-2092.

Swaminathan, "Steep Slope Devices: Enabling New Architectural Paradigms", Proceedings of the 51st Annual Design Automation Conference on Design Automation Conference, ISBN: 978-1-4503-2730-5, 2014, 1-6.

Yang, et al., "Site-Specific Two-Color Protein Labeling for FRET Studies Using Split Inteins", J. Am. Chem. Soc. vol. 131, 2009, 11644-11645.

PCT/US2015/040296 International Preliminary Report on Patentability, dated Jan. 26, 2017.

Rothberg, J., et al., "An integrated semiconductor device enabling non-optical genome sequencing", Nature, vol. 475, Jul. 21, 2011, 348-352.

\* cited by examiner

BIOCHEMICALLY ACTIVATED ELECTRONIC DEVICE

This application is a continuation of U.S. patent application Ser. No. 14/798,762 filed Jul. 14, 2015, which based on, and claims the benefit of, U.S. Provisional Application No. 62/171,523, filed Jun. 5, 2015; U.S. Provisional Application No. 62/161,709, filed May 14, 2015; U.S. Provisional Application No. 62/069,198, filed Oct. 27, 2014; and U.S. Provisional Application No. 62/024,856, filed Jul. 15, 2014, each of which is incorporated herein by reference in its entirety.

BACKGROUND

This disclosure relates generally to biosensor-based detection, and more specifically to biosensors that can be used for nucleic acid sequencing.

Currently available commercial platforms for sequencing DNA are relatively costly. The majority of these platforms use a 'sequencing-by-synthesis' approach, so called because DNA polymers are synthesized while detecting the addition of each monomer (i.e. nucleotide) to the growing polymer structure. Because a template DNA strand strictly directs synthesis of a new DNA polymer, one can infer the sequence of the template DNA from the series of nucleotide monomers that were added to the growing strand during the synthesis. Monitoring the reaction uses relatively expensive hardware such as lasers, detection optics and complex fluid delivery systems. The most successful commercial platforms to date also require expensive reagents and hardware to amplify the DNA templates before sequencing-by-synthesis can even begin. The complexity and expense of these platforms has hindered their use in some clinical and research contexts where there is a clear need for DNA sequencing technology.

Thus, there exists a need for improvements to nucleic acid sequencing platforms to make them more cost effective, rapid and convenient. The present disclosure addresses this need and provides other advantages as well.

BRIEF SUMMARY

The present disclosure provides a first method of nucleic acid sequencing. The method can include the steps of (a) providing a polymerase tethered to a solid support charge sensor; (b) providing one or more labeled nucleotides, whereby the presence of the label can be detected by the charge sensor when the label is in proximity to the charge sensor; and (c) detecting incorporation of the labeled nucleotide into a nascent strand complementary to a template nucleic acid.

The present disclosure also provides a method for attaching reaction components to charge sensors. The method can include the steps of (a) providing a solid support including a plurality of charge sensors, wherein each of the charge sensors has a capacity to attach a plurality of reaction components; (b) providing a fluid containing a plurality of reaction components of a particular type; and (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; and (iii) reaction components of the particular type from the fluid attach to the charge sensors under conditions that result in a solid support where each of the charge sensors is attached to a single one of the reaction components.

In some embodiments the method for attaching reaction components to charge sensors can include the steps of (a) providing a solid support including a plurality of charge sensors, wherein each of the charge sensors has a capacity to attach a plurality of reaction components; (b) providing a fluid containing a plurality of reaction components of a particular type, wherein each of the reaction components of the particular type is bound to a repellant moiety; and (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; (iii) reaction components from the fluid attach to the charge sensors, and (iv) the repellant moiety bound to each of the reaction components prevents more than one of the reaction components in the plurality of reaction components from attaching to each of the charge sensors.

A method for attaching reaction components to charge sensors can include the steps of (a) providing a solid support including a plurality of charge sensors, wherein each of the charge sensors has a capacity to attach a plurality of reaction components; (b) providing a fluid containing a plurality of reaction components of a particular type; (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; and (iii) reaction components of the particular type from the fluid attach to the charge sensors, thereby forming modified charge sensors that are attached to multiple reaction components of the particular type from the fluid; and (d) removing one or more of the reaction components of the particular type from each of the modified charge sensors to leave a single one of the reaction components of the particular type attached to each of the modified charge sensors.

The present disclosure provides a method of detecting a nucleotide. The method can include the steps of (a) providing a nucleotide binding protein (e.g. a polymerase) tethered to a solid support charge sensor; (b) providing one or more labeled nucleotides, whereby the presence of the label can be detected by the charge sensor when the label is in proximity to the charge sensor; and (c) detecting binding of the labeled nucleotide to the protein using the charge sensor.

In particular embodiments, a method of nucleic acid sequencing can be performed by (a) providing a polymerase tethered to a solid support charge sensor; (b) providing one or more labeled nucleotides, whereby the presence of the label can be detected by the charge sensor when the label is in proximity to the charge sensor; and (c) detecting incorporation of the labeled nucleotide into a nascent strand complementary to a template nucleic acid using the charge sensor.

A method of nucleic acid sequencing provided by the present disclosure can include the steps of (a) providing a polymerase tethered to a solid support charge sensor; (b) providing one or more labeled nucleotides, whereby the presence of the label can be detected by the charge sensor when the label is in proximity to the charge sensor, wherein the one or more labeled nucleotides have reversible terminator moieties; (c) detecting incorporation of the one or more labeled nucleotides into a nascent strand complementary to a template nucleic acid using the charge sensor, thereby forming a reversibly terminated nascent strand; (d) modifying the reversible terminated nascent strand to render the nascent strand capable of further incorporation of nucleotide; and (e) repeating (b) through (d) to obtain a sequence of the template nucleic acid.

Also provided is a method of nucleic acid sequencing that includes the steps of (a) providing a polymerase tethered to a solid support charge sensor; (b) contacting the polymerase with a template nucleic acid and one or more different nucleotide types under conditions wherein the polymerase catalyzes addition of the one or more nucleotide types to form a nucleic acid complement of the nucleic acid template, and wherein the addition of one or more different nucleotide types produces a conformational signal change from the polymerase that is detected by the charge sensor; (c) detecting a change in the signal from the polymerase using the charge sensor; and (d) determining the rate, polarity, amplitude or time duration for the change in the signal for the addition of the one or more different nucleotide type, thereby determining a sequence of nucleotides for the template nucleic acid.

DETAILED DESCRIPTION

Embodiments of the present disclosure relate generally to apparatus, compositions and methods for single molecule detection useful in applications such as nucleotide incorporation events detected in nucleic acid sequencing procedures. There is a need for improved detection systems which provide long sequencing reads in high-throughput manner Embodiments of the invention set forth herein satisfy this need and provide other advantages as well.

Complementary metal-oxide-semiconductor (CMOS)-based sensing schemes have been used for nucleic acid sequencing. Current CMOS-based sensing schemes exploit electrochemical detection of the by-products of the DNA polymerization that occurs in an SBS reaction (e.g. either protons or pyrophosphate). These methods provide advantages of being lightless and label-free. Being lightless, the reactions do not require expensive optics for detection. Cost and complexity of preparing reagents is typically reduced when label free reagents are used. However, disadvantages of current CMOS-based sensing schemes are that the reaction by-products, that are to be detected, are mobile and have a natural tendency to diffuse away from the reaction zone, which can result in cross-talk between neighboring sites when attempting to perform multiplexed sequencing reactions. Given the large size of most genomes and the limited read length for typical sequencing reactions, multiplexing is very important to achieve desired coverage levels for research and clinical applications of sequencing technology.

Figure 1:
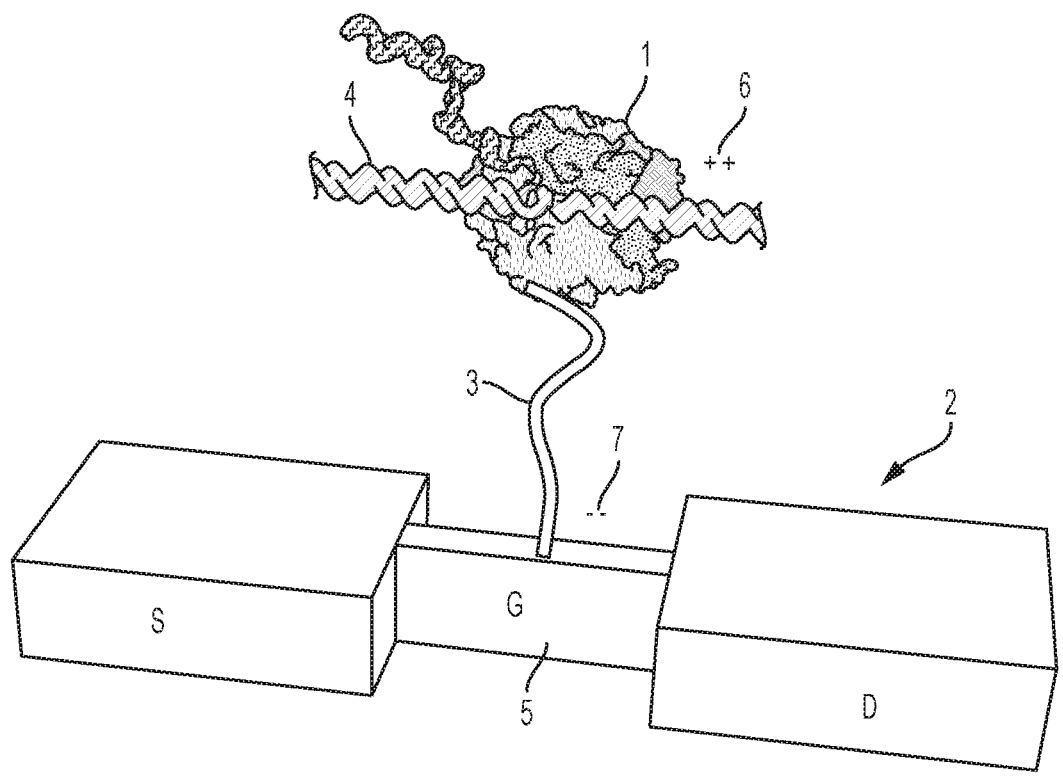
FIG. 1 shows a polymerase attached to a charge sensor via a tether.

The present disclosure provides a unique detection modality that can be used for nucleic acid sequencing and for detection of nucleic acids and other analytes in general. An exemplary embodiment is shown in FIG. 1. Briefly, polymerase 1 is immobilized on the gate 5 of a silicon nanowire field-effect transistor (FET) 2 with a tether 3. Optionally, the nanowire can be made of material other than silicon or the nanowire can be replaced with a nanotube. Optionally, tether 3 can be a conductive polymer strand, as indicated by the positive charge 6 at the end of the tether that is proximal to the polymerase and the negative charge 7 at the end of the tether that is distal to the polymerase and attached to the gate 5. The ssDNA 4 to be sequenced is bound to polymerase 1 after having been introduced in solution along with nucleotides and other reactants. As the complimentary strand is synthesized, disturbances in the charge distribution in the vicinity of the FET 2 are generated, either as a result of conformational changes of the polymerase 1, or due to presence of the nucleotides, possibly modified with an electrically active tag in the vicinity of the FET 2. Those modifications in the charge distribution are sensed by the nanowire-FET 2 and detected as a modulation in the FET transconductance current.

Some advantages of the FET-based apparatus and methods set forth herein are: (1) single-molecule sensitivity can be achieved with a properly scaled FET (2) high degree of parallelization (also called "multiplexability") is facilitated since the detected charge disturbance is localized in the vicinity of the polymerase, thereby avoiding cross-talk between neighboring FET sites (3) the optional use of a conducting tether assists in transmitting the charge disturbance to the gate and minimizes the undesirable effects of screening from the biological solution and (4) silicon nanowire FET can be conveniently manufactured using processes that are compatible with semiconductor manufacturing facilities.

Terms used herein will be understood to take on their ordinary meaning unless specified otherwise. Examples of several terms used herein and their definitions are set forth below.

As used herein, the term "array" refers to a population of charge sensors or molecules that are attached to one or more solid-phase substrates such that the charge sensors or molecules can be differentiated from each other according to their relative location. An array can include different molecules that are each located at a different addressable location (e.g. at different charge sensors) on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acid primers, nucleic acid probes, nucleic acid templates or nucleic acid enzymes such as polymerases and exonucleases.

As used herein, the term "attached" refers to the state of two things being joined, fastened, adhered, connected or bound to each other. For example, a reaction component, such as a polymerase, can be attached to a solid phase component, such as a charge sensor, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "charge sensor" is intended to mean a detection device that translates perturbations at its surface or in its surrounding electrical field into an electrical signal. For example, a charge sensor can translate the arrival or departure of a reaction component into an electrical signal. A charge sensor can also translate interactions between two reaction components, or conformational changes in a single reaction component, into an electrical signal. An exemplary charge sensor is a field effect transistor (FET) such as a carbon nanotube (CNT), single-walled carbon nanotube (SWNT) based FET, silicon nanowire (SiNW) FET, graphene nanoribbon FET (and related nanoribbon FETs fabricated from 2D materials such as MoS2, silicene, etc.), tunnel FET (TFET), and steep subthreshold slope devices (see, for example, Swaminathan et al., Proceedings of the 51st Annual Design Automation Conference on Design Automation Conference, pg 1-6, ISBN: 978-1-4503-2730-5 (2014) and Ionescu et al., Nature 479, 329-337 (2011)). Examples of FET and SWNT sensors that can be used in the methods and apparatus of the present disclosure are set forth in US Pat. App. Pub. No. 2013/0078622 A1, which is incorporated herein by reference in its entirety.

As used herein, the term "cleavable tether" is intended to mean a chemical linker having a bond that can be selectively broken by a chemical or physical treatment. Generally, the bond breakage is selective with respect to the chemical or physical treatment not having a substantial adverse effect on other reaction components that are present. A cleavable tether can be susceptible to selective bond breakage with agents such as, but not limited to, light, base, acid, heat, enzymes and chemical reagents. Electric field and physical agitation can also be used to cleave the tether. In a preferred embodiment the linker is a nucleotide linker. In some cases the linker comprises a site for cleavage by a sequence specific restriction endonuclease. However, sequence specific cleavage sites need not be present in some linkers used in accordance with methods set forth herein.

As used herein, the term "concatameric repeat" is intended to mean a serially repeating string of a particular nucleotide sequence in a single nucleic acid molecule. Concatameric repeats can be produced, for example, by rolling circle amplification (RCA) whereby the repeated nucleotide sequence is the complement of the template that is replicated by RCA.

As used herein, the term "conducting tether" is intended to mean a chemical linker through which electricity can be conducted or through which the electrical effects of an electric field can be transmitted. A conducting tether can be used to chemically link a reaction component to a charge sensor and to conduct electricity between the reaction component and the charge sensor. Exemplary conducting tethers include, but are not limited to, those having a doped polythiophene, poly(3,4-ethylenedioxythiophene), polyacetylene, polypyrrole, polyaniline, polyfluorene, polyphenylene, polypyrene, polyazulene, polynaphthalenes, polycarbazole, polyindole, or polyazepine structure. Linkers that can be useful as conducting tethers are also set forth in US Pat. App. Pub. No. 2010/0073847 A1, which is incorporated herein by reference in its entirety.

As used herein, the term "conformational signal change" means the appearance, disappearance, or alteration of a detectable signal from a molecule in response to a change in the structure, shape or arrangement of parts of the molecule. For example, the signal change can be due to a change in the interaction of a label with a first portion of the molecule to interact with a second portion of the molecule. The term, when specifically recited, is intended to distinguish from changes in signal that arise from a label of a molecule due to a change in the interaction of the label with a reactant that binds specifically to the molecule or a change in the interaction of the label with a product that results from catalytic activity of the molecule.

As used herein, the term "conformationally labeled," when used in reference to a molecule, means having at least one label that is responsive to a change in the structure of the molecule, a change in the shape of the molecule or a change in the arrangement of parts of the molecule. The molecule can be, for example, a polymerase, reverse transcriptase, exonuclease or other nucleic acid enzyme such as those set forth herein below. The parts of the molecule can be, for example, atoms that change relative location due to rotation about one or more chemical bonds occurring in the molecular structure between the atoms. The parts of the molecule can be domains of a macromolecule such as those commonly known in the relevant art. For example, polymerases include domains referred to as the finger, palm and thumb domains. In the case of proteins the parts can be regions of secondary, tertiary or quaternary structure. The label(s) can be attached to the molecule, for example, via a covalent linkage. However, the label(s) need not be attached to the molecule, being, for example, located in proximity to the molecule. In particular embodiments the label is not attached to a reactant or product of the molecule such as a nucleotide or nucleic acid.

As used herein, the term "different", when used in reference to nucleic acids, means that the nucleic acids have nucleotide sequences that are not the same as each other. Two or more different nucleic acids can have nucleotide sequences that are different along their entire length. Alternatively, two or more different nucleic acids can have nucleotide sequences that are different along a substantial portion of their length. For example, two or more different nucleic acids can have target nucleotide sequence portions that are different for the two or more molecules while also having a universal sequence portion that is the same on the two or more molecules. The term "different" can be similarly applied to other molecules, such as polymerases and nucleic acid enzymes.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "fluidic communication," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic communication can occur when there are no barriers that prevent the molecule from entering the site, contacting the site, separating from the site and/or exiting the site. However, fluidic communication is understood to exist even if diffusion is retarded, reduced or altered so long as access is not absolutely prevented.

As used herein, the term "label," when used in reference to a reaction component, is intended to mean a detectable reaction component or detectable moiety of a reaction component. A useful label is a charge label (also called a charge tag) that can be detected by a charge sensor. A label can be intrinsic to a reaction component that is to be detected (e.g. a charged amino acid of a polymerase) or the label can be extrinsic to the reaction component (e.g. a non-naturally occurring modification of an amino acid). In some embodiments a label can include multiple moieties having separate functions. For example a label can include a linker component (such as a nucleic acid) and a charge tag component.

As used herein, the term "non-natural," when used in reference to a moiety of a molecule, is intended to refer to a moiety that is not found attached to the molecule in its natural milieu or in a biological system unperturbed by human, technical intervention. Typically, non-natural moieties are synthetic modifications of molecules that render the molecules structurally or chemically distinct from the unmodified molecule or from molecules having natural modifications. As used herein, the term "non-natural," when used in reference to an analog used for a process, is intended to mean an analog that is not found in the natural milieu where the process occurs. Typically, non-natural analogs are synthetic analogs that are structurally or chemically distinct from other types of molecules in the class to which the analog belongs.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art.

As used herein, the term "nucleotide" is intended to include natural nucleotides, analogs thereof, ribonucleotides, deoxyribonucleotides, dideoxyribonucleotides and other molecules known as nucleotides. The term can be used to refer to a monomeric unit that is present in a polymer, for example to identify a subunit present in a DNA or RNA strand. The term can also be used to refer to a molecule that is not necessarily present in a polymer, for example, a molecule that is capable of being incorporated into a polynucleotide in a template dependent manner by a polymerase. The term can refer to a nucleoside unit having, for example, 0, 1, 2, 3 or more phosphates on the 5' carbon. For example, tetraphosphate nucleotides and pentaphosphate nucleotides can be particularly useful. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides also referred to herein as nucleotide analogs, include those that are not present in a natural biological system or not substantially incorporated into polynucleotides by a polymerase in its natural milieu, for example, in a non-recombinant cell that expresses the polymerase. Particularly useful non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties that can be used are described, for example, in U.S. Pat. Nos. 7,427,673; 7,414,116; and 7,057,026 and PCT publications WO 91/06678 and WO 07/123744, each of which is incorporated herein by reference in its entirety. It will be understood that in some embodiments a nucleotide analog having a 3' terminator moiety or lacking a 3' hydroxyl (such as a dideoxynucleotide analog) can be used under conditions where the polynucleotide that has incorporated the nucleotide analog is not further extended. In some embodiments, the nucleotide(s) will not include a reversible terminator moiety, or the nucleotides(s) will not include a non-reversible terminator moiety or the nucleotide(s) will not include any terminator moiety at all. Nucleotide analogs with modifications at the 5' position are also useful.

As used herein, the term "protection moiety" is intended to mean a compound or portion thereof that is attached to a reaction component to prevent the reaction component from undergoing a particular reaction. For example, a nucleic acid molecule can be bound to a nucleic acid enzyme such that the nucleic acid molecule prevents the nucleic acid enzyme from degradation or modification by a treatment that would otherwise cause degradation or modification of the enzyme. An antibody can also serve to bind a reaction component to protect the reaction component from degradation, inactivation or other reaction.

As used herein, the term "reaction component" is intended to mean a molecule that takes part in a reaction. Examples include, reactants that are consumed in a reaction, products that are created by a reaction, catalysts such as enzymes, that facilitate a reaction, solvents, salts, buffers and other molecules.

As used herein, the term "repellant moiety" is intended to mean a molecule or portion thereof that will occupy a space to prevent or inhibit occupancy of another molecule at the space or to inhibit juxtaposition of another molecule near the space. A repellant moiety can act via steric exclusion, charge repulsion, hydrophobic-hydrophilic repulsion or other forces.

As used herein, the term "terminator moiety," when used in reference to a nucleotide, means a part of the nucleotide that inhibits or prevents the nucleotide from forming a covalent linkage to a second nucleotide. For example, in the case of nucleotides having a pentose moiety, a terminator moiety can prevent formation of a phosphodiester bond between the 3' oxygen of the nucleotide and the 5' phosphate of the second nucleotide. The terminator moiety can be part of a nucleotide that is a monomer unit present in a nucleic acid polymer or the terminator moiety can be a part of a free nucleotide (e.g. a nucleotide triphosphate). The terminator moiety that is part of a nucleotide can be reversible, such that the terminator moiety can be modified to render the nucleotide capable of forming a covalent linkage to a second nucleotide. In particular embodiments, a terminator moiety, such as a reversible terminator moiety, can be attached to the 3' position or 2' position of a pentose moiety of a nucleotide analog.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus. Exemplary flow cells are set forth in further detail below.

As used herein, the term "type" (or "species") is used to identify molecules that share the same chemical structure. For example, a mixture of nucleotides can include several dCTP molecules. The dCTP molecules will be understood to be the same type or species as each other. Similarly, individual DNA molecules that have the same sequence of nucleotides are the same type or species.

The embodiments set forth below and recited in the claims can be understood in view of the above definitions.

The present disclosure provides apparatus, compositions and methods useful for single molecule detection in applications such as nucleotide incorporation events detected in nucleic acid sequencing procedures. The apparatus, compositions and methods set forth herein are particularly useful, for example, in single molecule nucleic acid sequencing reactions, such as sequencing by synthesis. However, it will be appreciated that the apparatus, compositions and methods set forth herein can be used for any other suitable detection schemes, including, but not limited to single molecule detection.

The present disclosure provides a first method of nucleic acid sequencing. The method can include the steps of (a) providing a polymerase tethered to a solid support charge sensor; (b) providing one or more labeled nucleotides, whereby the presence of the label can be detected by the charge sensor when the label is in proximity to the charge sensor; and (c) detecting incorporation of the labeled nucleotide into a nascent strand complementary to a template nucleic acid.

The polymerase used in the first method of nucleic acid sequencing can be tethered to the solid support charge sensor with a tether comprising nucleic acid. For example, the tether can comprise deoxyribonucleic acid (DNA), ribonucleic acid (RNA) or protein nucleic acid (PNA).

In some embodiments of the first method of nucleic acid sequencing, the labeled nucleotide is labeled at the γ-phosphate position of the nucleotide. The label can comprise an oligonucleotide and, optionally, the oligonucleotide is capable of hybridizing to an immobilized nucleic acid. Further optionally, the immobilized nucleic acid used in the first method of nucleic acid sequencing is part of a tether, the tether immobilizing a polymerase to the solid support charge sensor.

In some configurations of the first method of nucleic acid sequencing, the polymerase is held in proximity of less than 10, 9, 8, 7, 6, 5, 4, 3, 2, or 1 nm to the charge sensor.

In some embodiments of the first method of nucleic acid sequencing, the label is cleaved from the nucleotide after incorporation, for example, by the polymerase.

Optionally in the first method of nucleic acid sequencing, the one or more labeled nucleotides comprise a plurality of charge tags. For example, the one or more labeled nucleotides can comprise a unique charge tag for each of four types of nucleotides. The charge tag can be a negative charge tag, for example, comprising one or more of: a phosphate group, DMT and/or FMOC. Alternatively, the charge tag can be a positive charge tag, optionally comprising a primary amine.

The one or more labeled nucleotides in the first method of nucleic acid sequencing can comprise a plurality of different oligonucleotides (i.e. oligonucleotide moieties) capable of hybridizing to a plurality of immobilized tether sequences. Alternatively or additionally, a plurality of different oligonucleotides can be capable of hybridizing to a plurality of different locations within a particular tether used to immobilize a polymerase.

In some embodiments of the first method of nucleic acid sequencing, the one or more labeled nucleotides comprise 4 different charge tags and each of said labeled nucleotides comprises an oligonucleotide capable of hybridizing to the same immobilized tether sequence.

In some embodiments of the first method of nucleic acid sequencing, the polymerase tether and the labels on the labeled nucleotides contain deoxyribonucleotides that bind complementarily to each other, ribonucleotides that bind complementarily to each other, or deoxyribonucleotides that bind complementarily to ribonucleotides. For example, the polymerase tether and the labels on the labeled nucleotides can form a DNA:DNA duplex, RNA:RNA duplex or DNA:RNA heteroduplex. The deoxyribonucleotides or ribonucleotides can be nucleotide analogs that increase or modify duplex stability. For example, 2'-O-Methyl (2'-O-Me) or 2'-Fluoro (2'-F) modified ribonucleotides can be used. The 2'-O-me and 2'-F RNA modifications are known to increase the melting temperature of RNA:RNA duplexes by 0.5° C. to 1° C. per base pair, but result in only small changes in RNA:DNA stability (Majlessi et al., Nucleic Acids Res. 26:2224-9 (1998), incorporated herein by reference in its entirety). The increase in stability of the modified RNA:RNA base pairs can be used to accurately position the tag along the RNA tether as discussed below.

Moreover, the charge sensor can be functionalized with capture oligonucleotides and the labeled nucleotide can comprise an oligonucleotide label which hybridizes to one or more of the capture oligonucleotides in the first method of nucleic acid sequencing.

The charge sensor used in the first method of nucleic acid sequencing can comprise a nanowire FET. Optionally, the charge sensor comprises a carbon nanotube.

The charge sensor in the first method of nucleic acid sequencing can be part of an array of charge sensors.

The detecting step of the first method of nucleic acid sequencing can comprise detecting a plurality of incorporation events in succession.

The methods and apparatus set forth herein can provide long nucleic acid sequencing reads; fast reads; high throughput capability for sequencing; and a scalable platform for sequencing. In some embodiments, any compromises in single read accuracy can be mitigated by performing multiple overlapping reads due to the ability of the methods and apparatus set forth herein to provide throughput in the number of reads performed in parallel.

An exemplary sensor is shown in FIG. 1. Here a polymerase 1 creates a reaction site where nucleotides can be incorporated into a primed DNA template 4. The polymerase 1 is attached to a nanowire FET 2 via a tether 3. The apparatus provides single molecule sensitivity. Changes in charge distribution at the reaction site (e.g. polymerase conformation changes, nucleotide incorporation, arrival or departure of charged tags, changes in proximity of the polymerase to the charge sensor etc.) transmit to the gate and can be detected.

In particular embodiments, an apparatus or method of the present disclosure uses deeply scaled FinFET transistors as single-molecule charge sensors. FinFet sensors benefit from technology already under development by leading edge semiconductor manufacturers. Furthermore, previously published components can be used, including but not limited to (1) those used for immobilization of lysozyme on CNT to observe enzyme processivity in real time as described in Choi et al, Science, 335, 319 (2012), (2) those used to immobilize the Pol 1 Klenow fragment on CNT and observe DNA processivity in real time as described in Olsen et al, J. Amer. Chem. Soc., 135, 7885 (2013), (3) those used to elucidate a transduction mechanism as moving charged residues due to protein allosteric motion as described in Chi et al, NanoLett 13, 625 (2013). The present methods can also employ the apparatus, components of the apparatus, and methods set forth in US Pat. App. Pub. No. 2013/0078622 A1. Each of the above references is incorporated herein by reference in its entirety.

The apparatus and methods set forth in US Pat. App. Pub. No. 2013/0078622 A1 provide a Debye screening length of 1-2 nm in 50-100 mM NaCl. In this apparatus the allosteric motion must be near the attachment point of the polymerase to the transistor. Also, allosteric motion must be base-dependent to enable real-time discrimination of different types of nucleotides. Such resolution has not been previously demonstrated.

Figure 2:
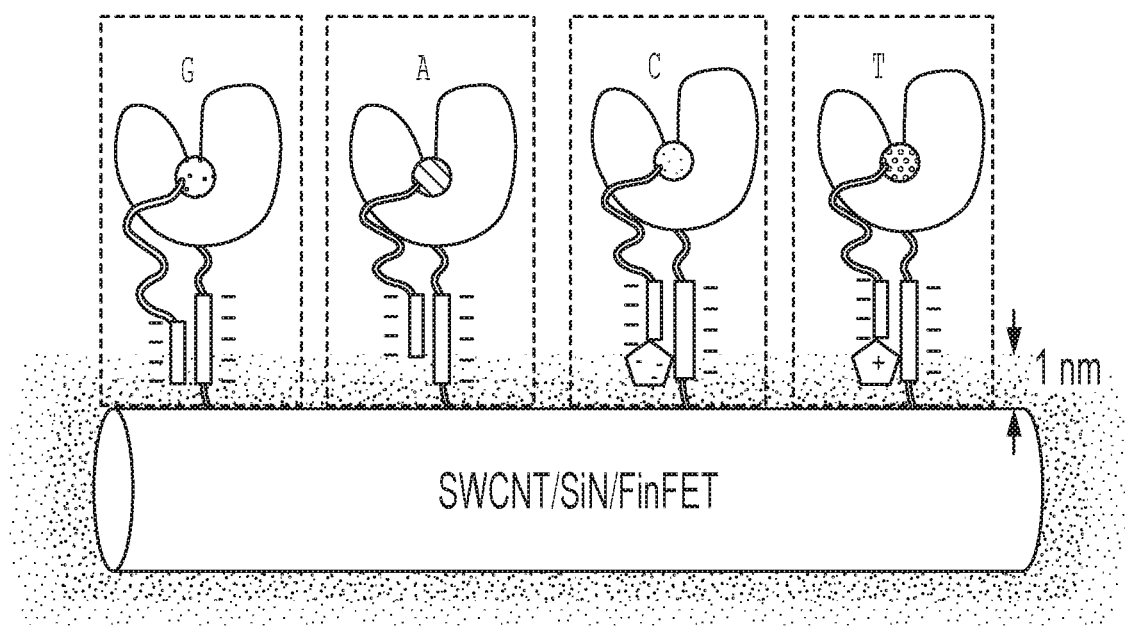
FIG. 2 shows polymerases attached to charge sensors via nucleic acid tethers and bound to nucleotides that can be distinguished based on charge or proximity to the sensor.

An embodiment that can be used to overcome limitations of some apparatus that utilize allosteric-based detection is diagrammed in FIG. 2. Here polymerase can be immobilized to a charge sensor such as a single walled carbon nanotube, silicon nanowire or FinFET. Immobilization can be via tethers that include DNA, RNA, PNA or analogs thereof. For convenience of demonstration the diagram shows four polymerases tethered to the charge sensor, each polymerase also being bound to a different gamma-phosphate labeled nucleotide type. As shown, nucleotides have an oligonucleotide moiety attached to the gamma-phosphate. A beta- or gamma-phosphate-labeled nucleotide that is properly matched to a template strand of a target nucleic acid will be held in place by a polymerase that is also bound to the template long enough to temporarily hybridize the oligonucleotide moiety to the tether (e.g. via Watson-Crick base complementarity). The hybridization causes the oligonucleotide moiety to perturb the field around the charge sensor which produces a detectable signal due to the change in transistor current through the charge sensor. The diagram shows the oligonucleotide moiety entering a field that is within 1-2 nm of the charge sensor. The properly matched beta- or gamma-phosphate-labeled nucleotide will be incorporated into a nascent strand that is hybridized to the template nucleic acid. This will, in turn, break the bond between the beta phosphate and the newly incorporated nucleotide. As a result, the oligonucleotide moiety (whether attached at the beta- or gamma-position of the nucleotide) is free to dehybridize from the tether and diffuse away from the charge sensor, thereby returning the field around the sensor to its unperturbed state. The appearance and disappearance of signal as the field around the charge sensor is perturbed and returned to the unperturbed state, respectively, can be correlated with incorporation of a nucleotide into the nascent strand of the target nucleic acid.

Particular embodiments can exploit synergistic binding of the gamma-phosphate labeled nucleotide to the polymerase and to the tether. The stability of the oligonucleotide moiety:tether complex can be relatively low such that the complex does not form for gamma-phosphate labeled nucleotide that are not also bound to polymerase (i.e. gamma-phosphate labeled nucleotides that are free in solution do not substantially bind to the tether). However, the synergistic effect of the affinities of the nucleotide moiety for the polymerase and the oligonucleotide moiety for the tether add up to allow substantial binding affinity overall. In some embodiments, the synergistic effect can exploit a combination of specific binding affinity between the nucleotide label and tether along with weak affinity produced by non-specific binding interactions. For example, specific binding can result from standard Watson-Crick base pairing and non-specific binding interactions can result from interactions of promiscuous bases (e.g. inosine) with native nucleotides. Thus, when the gamma-phosphate labeled nucleotide is bound to polymerase during incorporation, synergistic binding occurs which greatly increases the stability of the interaction between oligonucleotide moiety and tether. After the gamma phosphate is cleaved by the polymerase, the synergistic effect is lost and the oligonucleotide moiety will dissociate from the tether.

The type of nucleotide that is incorporated into the nascent strand at each position of the template strand can be determined based on unique properties of labels incorporated into each type of nucleotide. For example, four types of dNTPs can be distinguished by the position where the oligonucleotide moiety hybridizes to the tether, the length of the oligonucleotide moiety and/or the presence of a charged moiety on the label. FIG. 2 provides an example where four-state discrimination is achieved using 2 charge tags (other than the negatively charged phosphates of the oligonucleotide moiety) and two tether hybridization positions. Specifically, dCTP is uniquely labeled with a negatively charged extrinsic moiety, dTTP is uniquely labeled with a positively charged extrinsic moiety, dATP and dGTP are distinguished from the other two nucleotide types based on absence of any extrinsic charge moiety, and dATP is distinguished from dGTP based on differential proximity of the oligonucleotide moieties to the charge sensor when they are hybridized to the tether.

Figure 3:
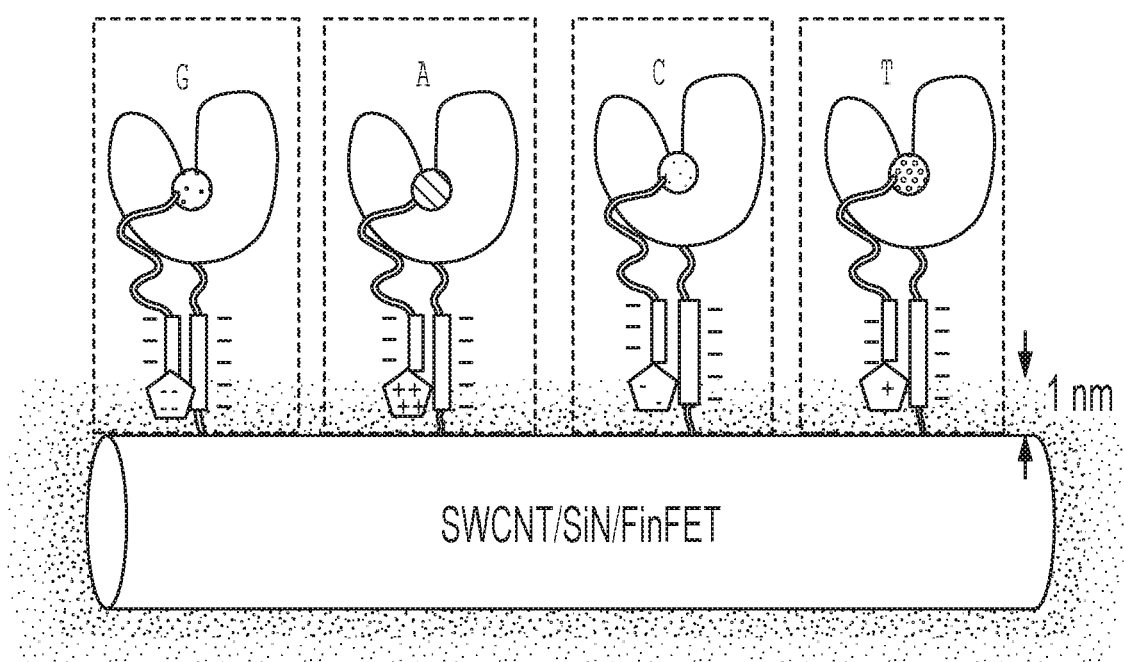
FIG. 3 shows polymerases attached to charge sensors via nucleic acid tethers and bound to nucleotides that can be distinguished based on charge.

It will be understood that different nucleotide types can be distinguished based on any of a variety of combinations of positive charge moieties, negative charge moieties and/or tether hybridization locations. Alternatively or additionally, the charge moieties used to distinguish different types of nucleotides can differ in the strengths of the charges, even if the charges have the same sign. The exemplary configuration shown in FIG. 3 provides four-state discrimination based on a single tether hybridization position and four different charge moieties. Specifically, dGTP and dCTP both contain negatively charged moieties that distinguish them from dATP and dTTP, and dGTP can be distinguished from dCTP due to charge that is distinguishably higher than the charge on dCTP. Similarly, dATP and dTTP can be distinguished from each other due to the higher positive charge on the dATP moiety compared to the dTTP moiety.

As noted previously herein, the precision of tag placement at specific hybridization positions along a tether can be enhanced through the use of a tether having ribonucleotides and a nucleotide label having 2'-O-Me and 2'F modified RNA bases. Alternative configurations can use a tether that contains 2'-O-Me and 2'F modified ribonucleotides with label having ribonucleotides, or both the tether and label can include a mixture of native ribonucleotides and 2'-O-Me and 2'F modified ribonucleotides. Although it is possible to use a tether and/or oligonucleotide moiety that is primarily composed of RNA, it may be desirable to use a DNA-based or PNA-based tether and/or oligonucleotide to avoid nuclease sensitivity that is associated with RNA. For example, a DNA-based or PNA-based tether and/or oligonucleotide can include native ribonucleotides or non-native ribonucleotide analogs to achieve binding advantages set forth herein while reducing risk of unwanted nuclease digestion. In further embodiments, the tether can include one or more deoxyribonucleotides that are complementary to ribonucleotides in a nucleotide label or alternatively the tether can include ribonucleotides that are complementary to deoxyribonucleotides in a nucleotide label.

Figure 10:
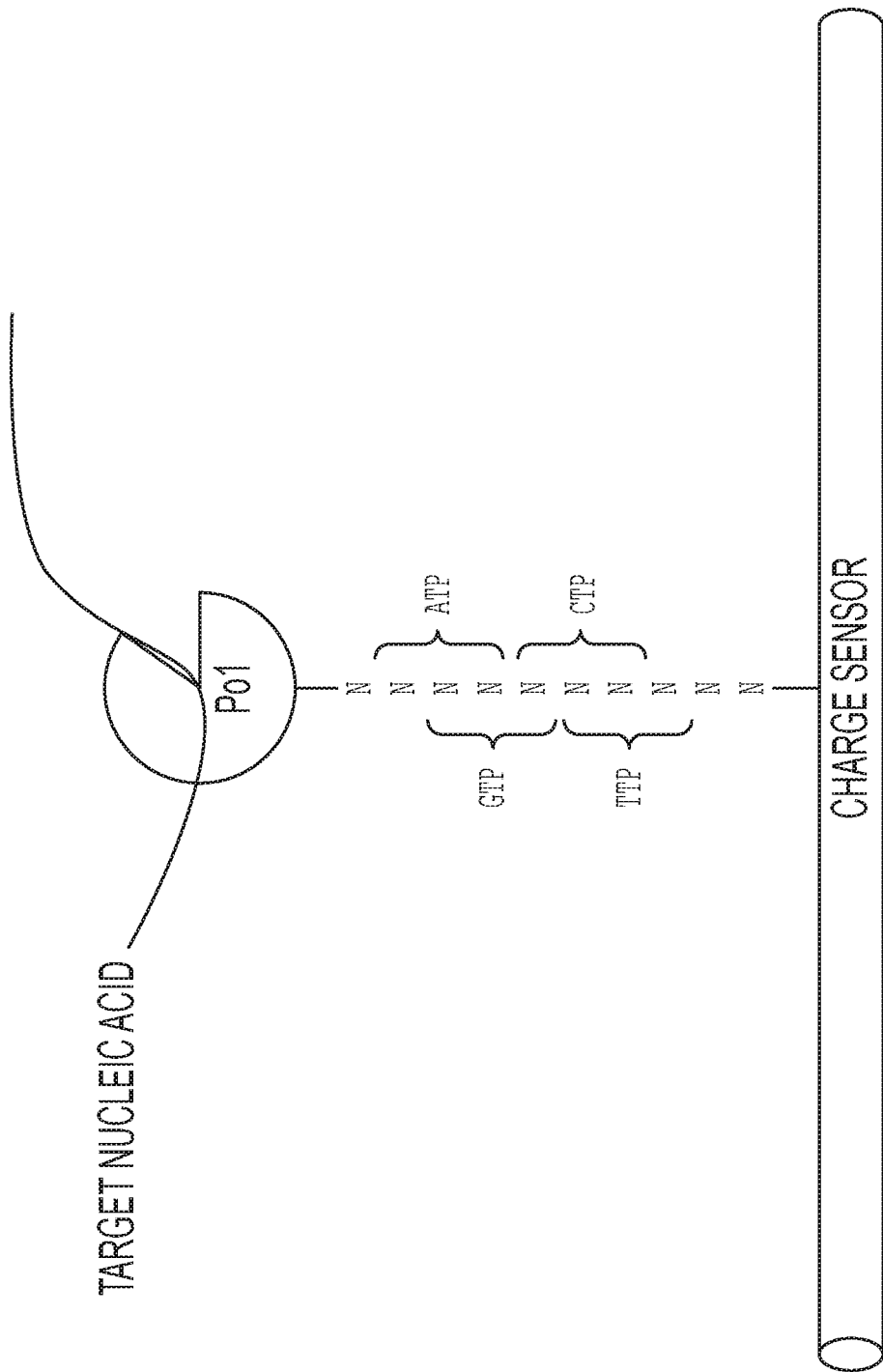
FIG. 10 shows a charge sensor that is attached to a polymerase (Pol) via a tether having a nucleic acid sequence (generically represented as a sequence of 10 Ns). The polymerase is complexed to a target nucleic acid and binding sites for labels associated with four different nucleotides (ATP, GTP, CTP and TTP, respectively) are indicated.

A tether that attaches a polymerase to a charge sensor can have different binding positions for different nucleotide analogs as set forth in several exemplary embodiments herein. The binding positions for two or more nucleotide analogs can overlap or they can be discrete with no overlap. For example, as shown in FIG. 10, the binding sites for ATP and GTP analogs overlap on the tether by 2 nucleotides (i.e. there is a 1 nucleotide offset between the two binding sites). For purposes of illustration, the tether sequence is depicted as a series of generic "N" nucleotides. Any of a variety of sequences can be used in accordance with rules of complementarity and desired hybridization strengths and specificities. As also shown in FIG. 10, the binding sites for ATP and TTP on the tether have no overlap, being discrete and separated by 1 nucleotide. Depending on the length of the tether, length of the binding sites and length of the oligonucleotide moieties on the nucleotide analogs, some, all or none of the binding sites on the tether can overlap.

Figure 11:
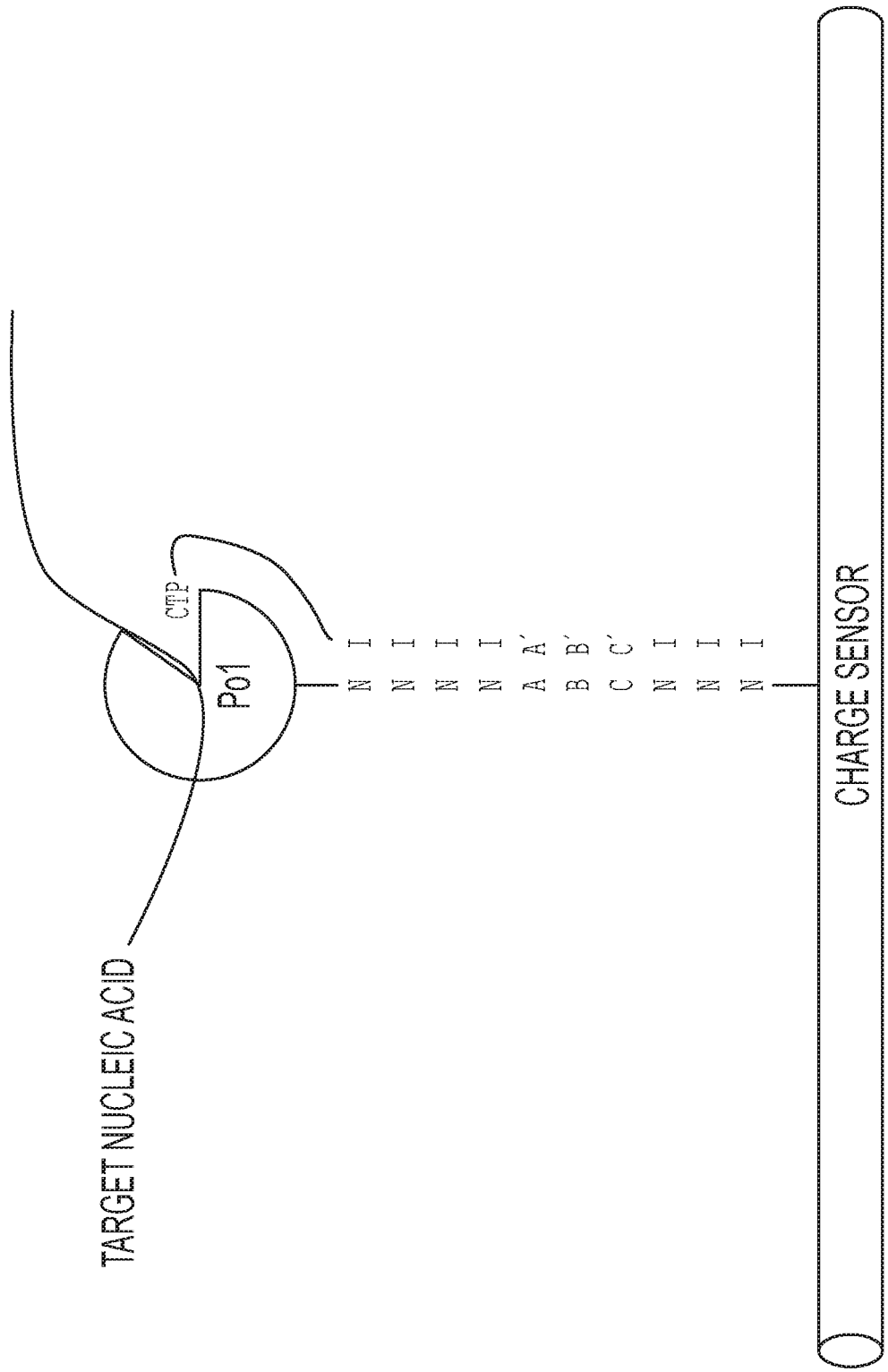
FIG. 11 shows a charge sensor that is attached to a polymerase (Pol) via a tether having a nucleic acid sequence (generically represented as a sequence of 10 Ns). The polymerase is complexed to a target nucleic acid and a labeled CTP analog. The label on the CTP analog includes a nucleic acid region having inosines (I) and a specificity region (A'B'C') that hybridizes to a complementary region on the tether (ABC).

The oligonucleotide moiety of a nucleotide analog can have a sequence of nucleotides that hybridizes specifically to a complementary sequence on a tether. In some embodiments the oligonucleotide moiety can also include promiscuous nucleotide positions that bind non-specifically to a tether. Such positions can provide a weak interaction between the oligonucleotide moiety and tether that facilitates the formation of a specific hybrid structure. For example, as shown in FIG. 11, an oligonucleotide moiety can include several inosines (I) that are known to bind promiscuously, albeit weakly, with all four native nucleotides of DNA. The oligonucleotide moiety and tether can form a weak complex via interactions between the inosines in the oligonucleotide moiety and the native nucleotides in the tether. This can allow the specific portions of the sequence (e.g. indicated as ABC and its complement A'B'C' in the figure) to associate more rapidly than they would have if required to diffuse absent formation of a weak complex. Furthermore, once a specific complex has formed the inosines can provide further stability.

The exemplary oligonucleotide moiety in FIG. 11 includes promiscuous nucleotide positions flanking both sides of the specific sequence. However, it will be understood that one or more promiscuous nucleotide positions can be located on only the 5' or 3' side of the specific sequence. Other examples of promiscuous nucleotide positions include those formed by degenerate oligonucleotide synthesis or those formed with other nucleotide analogs known in the art to hybridize promiscuously with 2 or more types of nucleotides.

In the examples shown in FIG. 10 and FIG. 11, as well as other examples set forth herein, the tether is a nucleic acid that hybridizes to an oligonucleotide moiety of a nucleotide analog. It will be understood that other binding partners can be used as tether and label moiety instead of the nucleic acids. The binding sites can be discrete or overlapping as exemplified above for nucleic acids. Also, the binding sites can include a combination of weak, non-specific interacting partners along with stronger, specific interacting partners.

Figure 12:
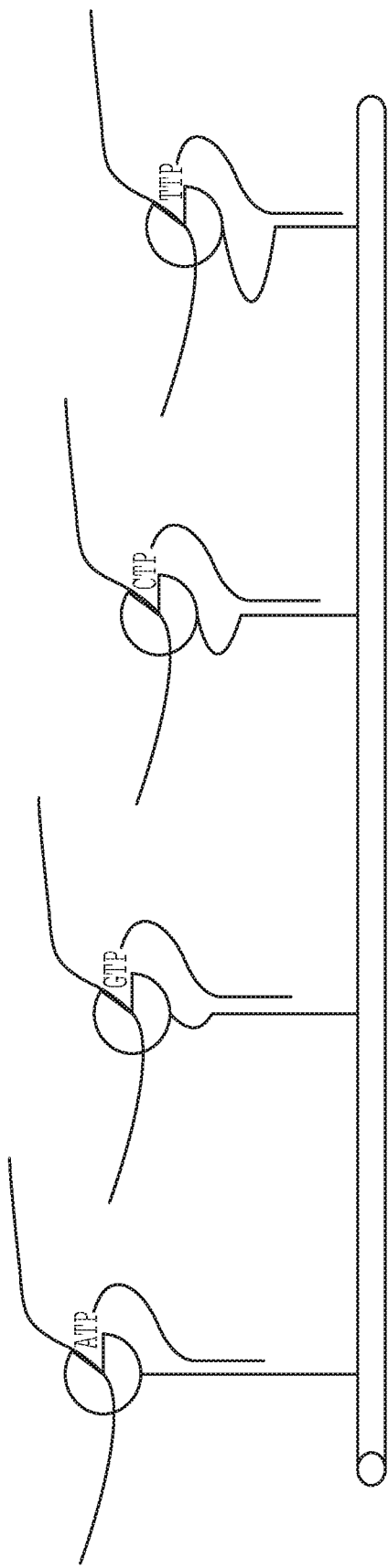
FIG. 12 shows a tethered polymerase in four different positional states relative to the charge sensor due to the binding of four different nucleotide analogs. Each of the nucleotide analogs has an oligonucleotide moiety of the same length as the other 3 nucleotide analogs, but each nucleotide analog has a specific binding sequence that binds to a different region of the tether compared to the regions where the other nucleotide analogs bind.

Several embodiments set forth herein have exemplified the use of a plurality of different nucleotide analogs having oligonucleotide moieties of differing lengths. In such embodiments, the different nucleotide types can be distinguished based on the different lengths of the oligonucleotide moieties. Alternatively, different nucleotide analogs can have oligonucleotide moieties of the same length. However, each nucleotide analog can have a specific binding sequence that binds to a different region of a tether compared to the regions where the other nucleotide analogs bind. An exemplary configuration is shown in FIG. 12 where binding of the polymerase to different nucleotide analogs places the polymerase in one of four distinguishable states. The oligonucleotide moiety for the ATP analog binds to a location on the tether that is nearest to the attachment point of the tether to the polymerase, the oligonucleotide moiety for the TTP analog binds to a location on the tether that is furthest from the attachment point of the tether to the polymerase, and the oligonucleotide moieties for the GTP and CTP analogs bind to respectively distinct locations on the tether that are at intermediate distances from the binding sites for the other two nucleotide analogs. As such, binding of the different nucleotide analogs to the polymerase will position the polymerase at different distances from the charge sensor (e.g. causing different size loops to form in the tether as shown in the figure). The different nucleotide types can be distinguished based on the differences in signals produced for the different distances of the polymerase from the sensor. In embodiments where one or more of the nucleotide analogs includes a charge tag or other detectable moiety (e.g. attached at the end of the oligonucleotide moiety that is distal to the nucleotide moiety), the binding between the oligonucleotide moiety and tether will position the detectable moiety at different distances from the charge sensor. In this case, the different nucleotide types can be distinguished based on the differences in signals produced for the different distances of the detectable moieties from the sensor.

Figure 4:
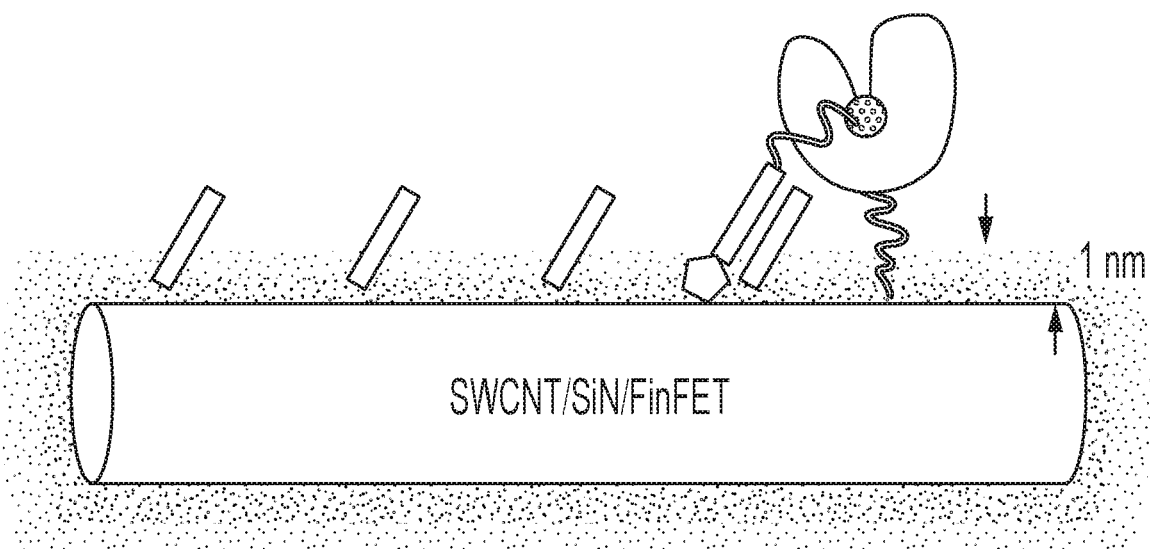
FIG. 4 shows a polymerase tethered to a charge sensor, wherein the charge sensor is also attached to a plurality of oligonucleotides capable of binding to labels on nucleotides.

As demonstrated by the embodiment diagrammed in FIG. 4, the tether that attaches polymerase to the charge sensor need not be capable of hybridizing to the tags present on the nucleotides. Rather, the charge sensor can be functionalized to attach one or more oligonucleotides that are complementary to one or more of the nucleotide types being detected. Discrimination of the different nucleotides can be achieved based on sign of the charge, strength of the charge, length of the oligonucleotide moiety that hybridizes to the surface attached oligonucleotide(s), or proximity/location on the surface attached oligonucleotide(s) where the oligonucleotide moiety hybridizes, or a combination thereof.

Advantages of several configurations set forth above include, for example, overcoming screening issues by placing charges within 1-2 nm of the gate with atomic precision, ability to achieve a higher level of current modulation through the use of charge tags, and opening up of the space of available polymerases since base-specific allosteric motion is not required for detection.

Figure 5:
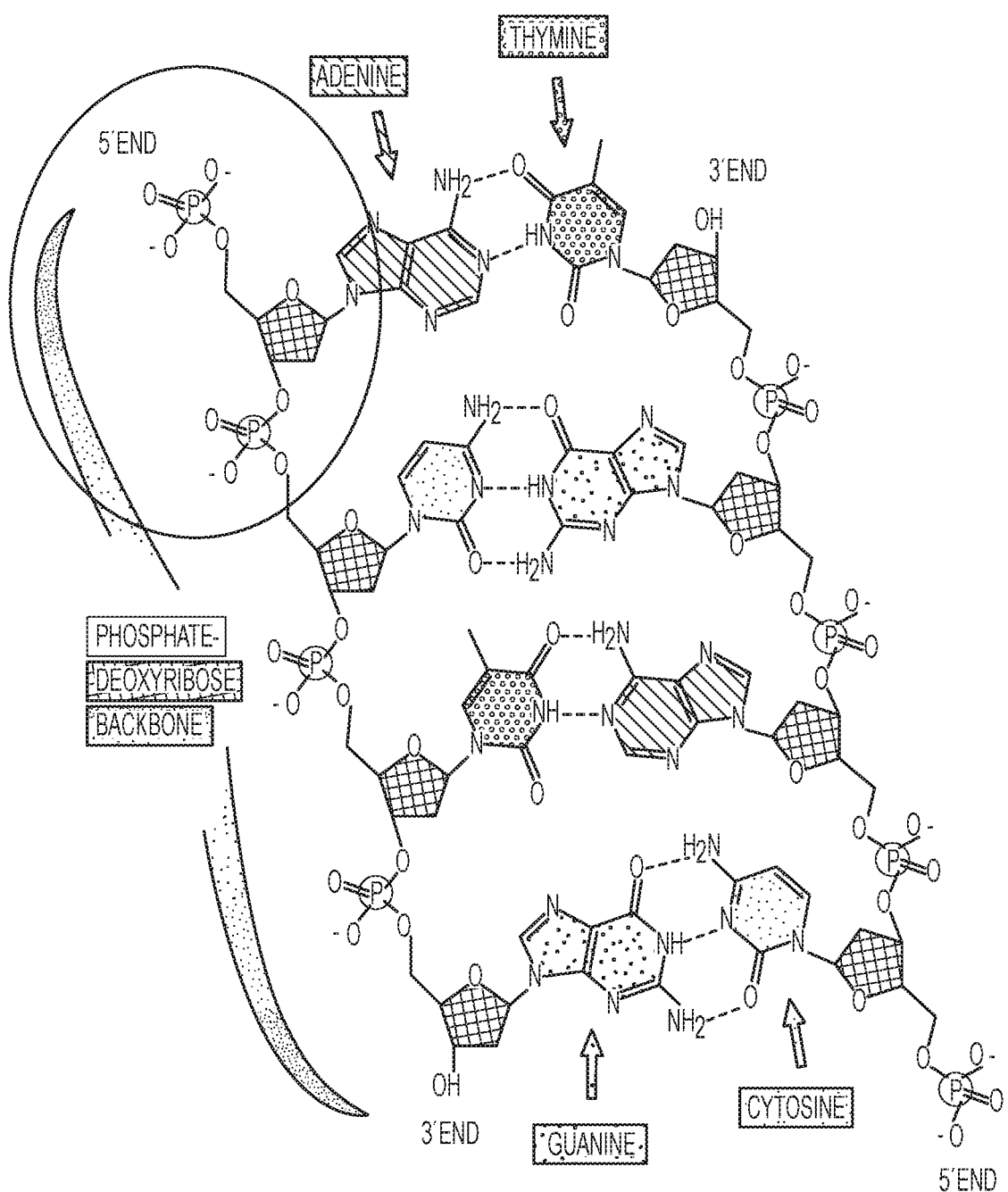
FIG. 5 shows a nucleotide label having two negatively charged oxygens at the end of an oligonucleotide moiety of the label.
Figure 6:
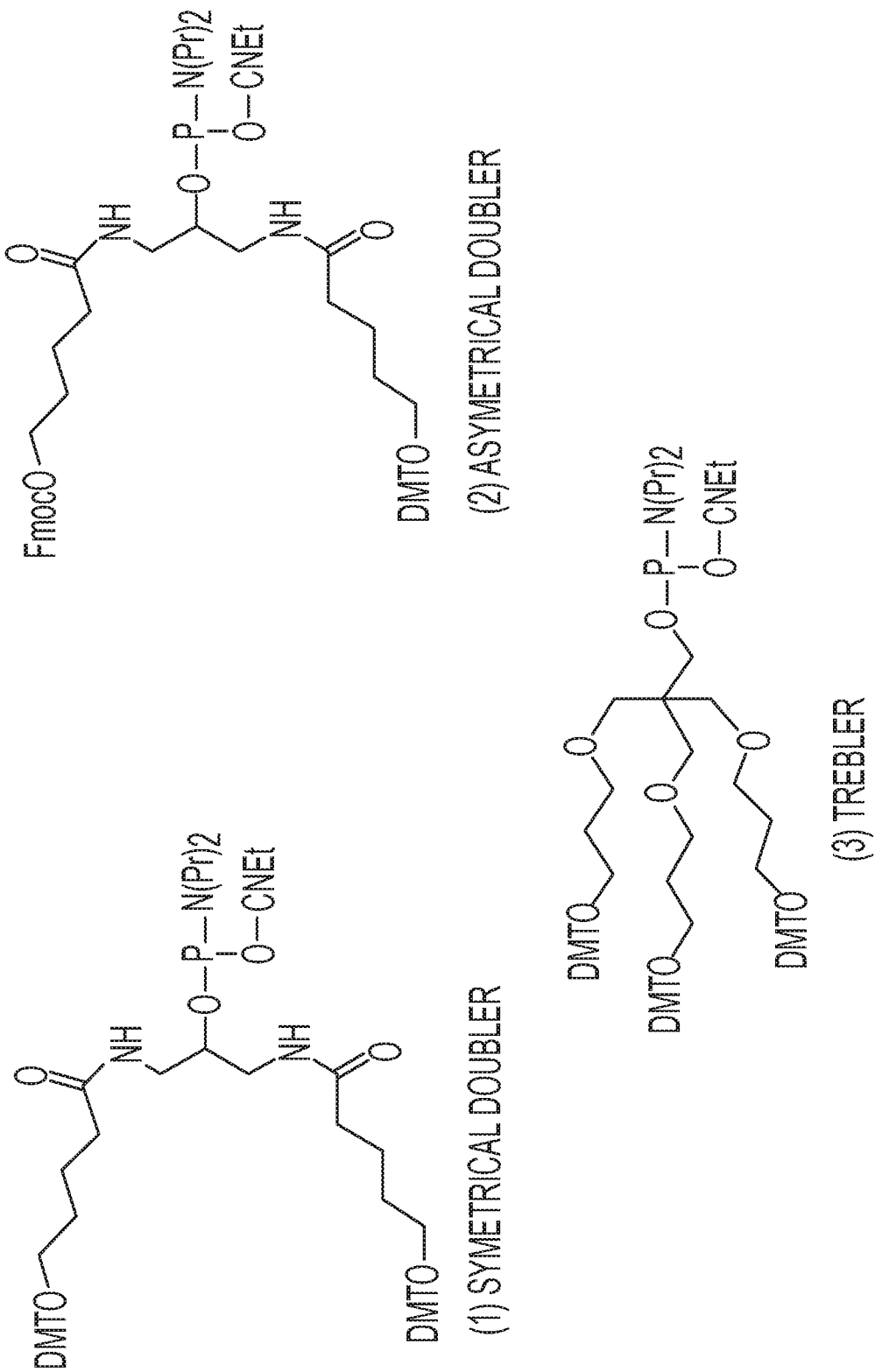
FIG. 6 shows charge tags that can be detected using a charge sensor.

An exemplary charge tag that can be useful in the apparatus and methods set forth herein is a phosphate moiety, for example, located at the 5' end of a nucleic acid moiety. This moiety can be readily added during available oligonucleotide synthesis protocols and will result in two negatively charged oxygens at the end of the oligonucleotide moiety as shown in FIG. 5. Chemical phosphorylation during oligonucleotide synthesis can be achieved by converting a DMT protecting group into a 5' phosphate group using 2-[2-(4,4' Dimethoxytrityloxy)ethylsulfonyl]ethyl-(2-cyanoethyl)-(N, N-diisopropyl)-phosphoramidite (available from Glen Research, Sterling Va., catalog No. CPR 10-1900). A series of charge tags having different numbers of negative charges can be made using Tris-2,2,2-[3-(4,4'-dimethoxytrityloxy) propyloxymethyl]ethyl-[(2-cyanoethyl)-(N,N-diisopropyl)]-phosphoramidite (available from Glen Research, Sterling Va., catalog No. 10-1922-xx), 1,3-bis-[5-(4,4'-dimethoxytrityloxy)pentylamido]propyl-2-[(2-cyanoethyl)-(N,N-diisopropyl)]-phosphoramidite (available from Glen Research, Sterling Va., catalog No. 10-1920-xx), 1-[5-4,4'-dimethoxytrityloxy)pentylamido]-3-[5-fluorenomethoxycarbonyloxypentylamido]-propyl-2[(2-cyanoethyl)-(N,N-diisopropyl)]-phosphoramidite (available from Glen Research, Sterling Va., catalog No. 10-1921-xx), or oligonucleotide dendrimers which contain various numbers of DMT (4,4'-dimethoxytrityl) or Fmoc (Fluorenylmethyloxycarbonyl) moieties, such as those available from Glen Research or shown in FIG. 6. A useful positively charged tag is 2-[2-(4-Monomethoxytrityl)aminoethoxy]ethyl-(2-cyanoethyl)-N,N-diisopropyl)-phosphoramidite (available from Glen Research, Sterling Va., catalog No. 10-1905-xx). Another useful positively charged moiety is a 5' primary amine which would have a single positive charge at the appropriate pH.

Table I provides a listing of useful modifications and charges that can be used as labels in an apparatus or method set forth herein.

TABLE I

| 5' Terminus | Reagents | Final Charge State |
|---|---|---|
| 5' OH | N/A | Neutral |
| 5' Phosphate | CPR 10-1900 (Glen Res.) | −2 |
| 5' Phosphate (x2) | CPR 10-1900 and symmetric doubler (Glen Res.) | −4 |
| 5' Phosphate (x3) | CPR 10-1900 and symmetric trebler (Glen Res.) | −6 |
| 5' primary amine | 5' amino-modifier 5 | +1 |

The present disclosure provides a method for attaching reaction components to charge sensors. The method can include the steps of (a) providing a solid support including a plurality of charge sensors, wherein each of the charge sensors has a capacity to attach a plurality of reaction components; (b) providing a fluid containing a plurality of reaction components of a particular type; and (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; and (iii) reaction components of the particular type from the fluid attach to the charge sensors under conditions that result in a solid support where each of the charge sensors is attached to a single one of the reaction components.

In some embodiments the method for attaching reaction components to charge sensors can include the steps of (a) providing a solid support including a plurality of charge sensors, wherein each of the charge sensors has a capacity to attach a plurality of reaction components; (b) providing a fluid containing a plurality of reaction components of a particular type, wherein each of the reaction components of the particular type is bound to a repellant moiety; and (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; (iii) reaction components from the fluid attach to the charge sensors, and (iv) the repellant moiety bound to each of the reaction components prevents more than one of the reaction components in the plurality of reaction components from attaching to each of the charge sensors.

A method for attaching reaction components to charge sensors can include the steps of (a) providing a solid support including a plurality of charge sensors, wherein each of the charge sensors has a capacity to attach a plurality of reaction components; (b) providing a fluid containing a plurality of reaction components of a particular type; (c) contacting the solid support with the fluid under conditions wherein (i) the plurality of reaction components of the particular type are in fluid communication with the plurality of charge sensors, (ii) a greater number of reaction components of the particular type is in the fluid than the number of charge sensors on the solid support; and (iii) reaction components of the particular type from the fluid attach to the charge sensors, thereby forming modified charge sensors that are attached to multiple reaction components of the particular type from the fluid; and (d) removing one or more of the reaction components of the particular type from each of the modified charge sensors to leave a single one of the reaction components of the particular type attached to each of the modified charge sensors.

Useful charge devices include analytical devices that can incorporate a reaction component in direct spatial contact with a transduction element in a way to allow the rapid and convenient conversion of reaction events to detectable signals. Devices based on field-effect transistors (FETs) can directly translate interactions between reaction components (e.g., polymerases) and the transistor surface into readable electrical signals. In a standard FET, current flows along a conducting path (the channel) that is connected to two electrodes, (the source and the drain). The channel conductance between the source and the drain is switched on and off by a third (gate) electrode that can be capacitively coupled through a thin dielectric layer.

In particular embodiments, FETs are configured to accomplish single molecule detection. More particularly, these charge sensors can be configured to monitor the dynamics of a single molecule reaction. Any type of conduction channel that is generally found in field effect transistors can be used in an apparatus or method set forth herein. Exemplary conduction channels are formed from metals, metal oxides, semiconductors, or nanometer-scale conductors such as nanowires, or graphene.

Particularly useful charge sensors for single molecule detection are single-walled carbon nanotubes (SWNTs). See, for example, Star et al., Nano. Lett. 3, 459 (2003); Star et al., Org. Lett. 6, 2089 (2004); Besterman et al., Nano. Lett. 3, 727 (2003); Gruner, Anal. Biooanal. Chem. 384, 322 (2005); Chen et al. Proc. Natl. Acad. Sci. U.S.A. 100, 4984 (2003) and US Pat App. Pub. No. 2013/0078622 A1, each of which is incorporated herein by reference in its entirety. SWNTs are extremely small conductors, typically on the order of about 1 nanometer in diameter.

A SWNT can be coated with a chemoselective polymer, metal or metal oxide nanoparticle, or reaction components like proteins, nucleic acids or antibodies. See for example, Besterman et al., Nano. Lett. 3, 727 (2003); and Chen et al. Proc. Natl. Acad. Sci. U.S.A. 100, 4984 (2003). Single reaction components can be attached to these SWNT and other charge sensors using methods set forth herein.

In some embodiments a single reaction component can be attached to a charge sensor by creating one single covalent defect on the charge sensor, for example, using techniques set forth in Goldsmith et al. Science 315, 77 (2007), which is incorporated herein by reference in its entirety. For example a SWNT can be produced having a single defect such that a variety of attachment chemistries can be used to link a single reaction component to the reactive defect site selectively, without coating the rest of the SWNT with additional reaction components. SWNTs can also be attached to reaction components by non-covalent means, for example, using techniques set forth in Chen et al, J. Am. Chem. Soc. 123, 3838 (2001), which is incorporated herein by reference in its entirety. These methods can be modified as set forth herein to reliably bind a single reaction component non-covalently to a SWNT.

SWNTs are semiconductors with electronic bandgaps that can vary from 1 electron volt to effectively zero. SWNTs are useful as conduction channels because single molecule sensing devices can be fabricated from SWNT wires of any type, with or without gate electrodes, and on glass, plastic, or silicon substrates. Useful SWNTs and their configurations for single molecule detection are set forth in US Pat App. Pub. No. 2013/0078622 A1, which is incorporated herein by reference in its entirety.

Other charge sensors that can be modified for use in an apparatus or method set forth herein include, without limitation, silicon nanowire (SiNW) FET, FET made of III-V materials, silicon FinFET, graphene nanoribbon FETs as well as nanoribbon FETs from other 2D materials such as $MoS_2$ and silicene, tunnel FET (TFET), and steep subthreshold slope devices (see, for example, Swaminathan et al., *Proceedings of the 51st Annual Design Automation Conference on Design Automation Conference*, pg 1-6, ISBN: 978-1-4503-2730-5 (2014) and Ionescu et al., *Nature* 479, 329-337 (2011)). Carbon nanotubes can also be useful.

A plurality of charge sensors can be provided in the form of an array of charge sensors. The array can include at least 10, 100, $1 \times 10^3$, $1 \times 10^4$, $1 \times 10^4$, $1 \times 10^4$ or more charge sensors. Each individual charge sensor can be located at a discrete location in the array that is separated from the other charge sensors in the array. For example, each charge sensor can reside in a well or depression in a solid support. The locations, even when separated from each other, can optionally be in fluid contact with a bulk solution. In such a configuration, multiplex reactions can occur on the array of charge sensors by delivering common reagents to all of the charge sensors via bulk fluid delivery. Taking nucleic acid sequencing reactions as an example, nucleotides can be delivered via bulk solution to an array of wells (or other features), each well (or other feature) hosting an individual sequencing reaction. The nucleotide delivery will result in parallel sequencing reactions at the wells (or other features).

A charge sensor, such as a Si nanowire can have dimensions that are less than 10 nm wide and greater than 100 nm long. A Si nanowire or other charge sensor can be placed in a well that is 10 nm×10 nm, 50 nm×100 nm or larger. For example, a well within which a charge sensor resides can have an opening on a surface that is at least 100 $nm^2$, 1000 $nm^2$, 5000 $nm^2$, $1 \times 10^4$ $nm^2$, or larger. The circuitry to read out the signal from the charge sensing element can occupy an area of the solid support that is 1 micron×1 micron or larger.

In some embodiments, a charge sensor will have a uniform width along the entire length. Alternatively, a charge sensor can have substantial variable width along its length. For example, a charge sensor can include a region of relatively narrow width, akin to a 'pinched' region. The width of the pinch region can have a diameter that is, for example, 75%, 50%, 40%, 30%, 20% or 10% of the diameter of the relatively larger width regions of the charge sensor. The pinch can provide the advantage of increasing the effect of a polymerase's charged residue motion on the sensor. A further benefit is relaxed tolerances for channel fabrication and opening/alignment of the first layer dielectric passivation of the FET sensor. For example a charge sensor having a 20 nm diameter with a 10 nm pinched area can be particularly useful. Other dimensions for a charge sensor with a pinched region include, for example diameters of at least 25, 30, 35, or 40 nm or more with a pinched region that is at most 10, 20, 30, 40, or 50 nm long. Sensors having smaller diameters can also be used for example those having diameters of at least 5, 10, 15, or 20 nm can have a pinched region with a length in the exemplified range. It will be understood that in some embodiments the maximum diameter of a charge sensor will be 50 nm, 40 nm, 30 nm, 20 nm 10 nm or less.

A tether for a polymerase or other enzyme can be attached to a pinched region or at a point that is proximal to the pinched region. Thus, the tether can be placed to localize a polymerase or other enzyme in proximity to the pinched region.

Figure 8:
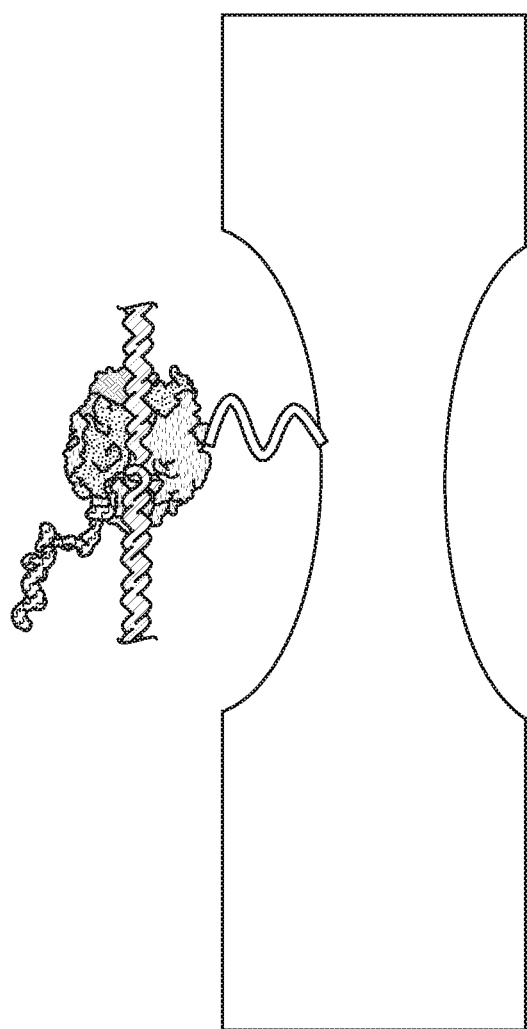
FIG. 8 shows a charge sensor having a pinched region and a polymerase tethered to the charge sensor at the pinched region. The polymerase is complexed with a template strand and nascent strand of a nucleic acid.

An exemplary implementation of a charge sensor having a pinched region is shown in FIG. 8. The pinched region can be fabricated via appropriate lithographic mask design where the shape of the mask is such that it produces the desired pinch. Alternatively, proximity effects during lithographic patterning may be used to locally pinch the charge sensor by placing electrodes orthogonal to the sensor in close proximity to the region to be pinched. In addition to producing the desired pinch, the proximity electrodes can be used to produce an electrophoretic force that positions the enzyme at the pinch region.

Figure 9:
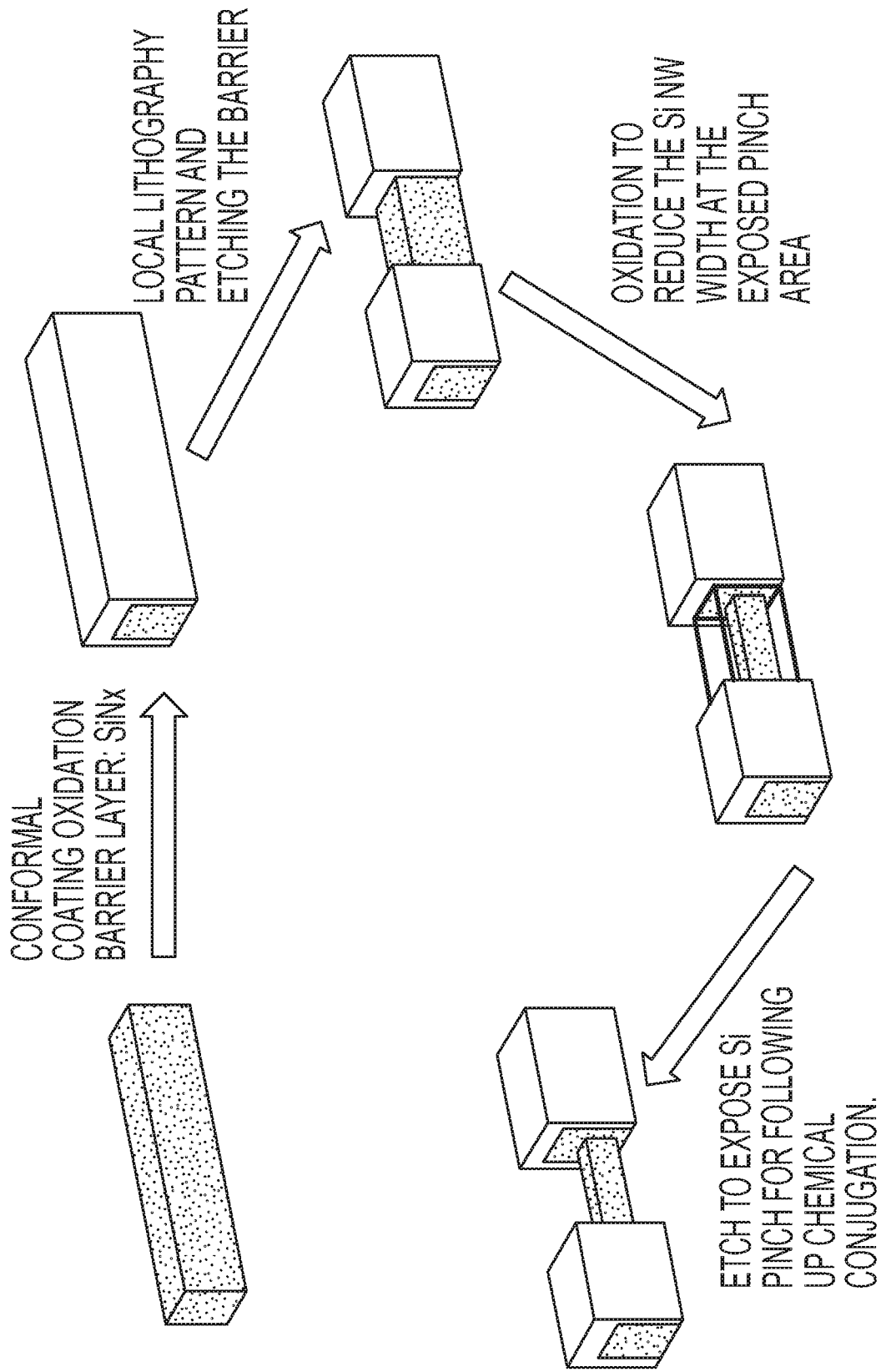
FIG. 9 shows a diagrammatic representation for a method of introducing a pinch into silicon using local oxidation.

Another exemplary implementation is shown in FIG. 9. Here a pinch is introduced into silicon using local oxidation. In a first step a silicon wire is coated with an oxidation barrier, such as Silicon Nitride (SiNx). A region of the silicon wire can be exposed using local lithography to etch away the oxidation barrier. Then the partially coated wire can be oxidized to reduce the width of the silicon wire at the exposed region. Further etching can be carried out to expose the silicon pinch for chemical conjugation.

Those skilled in the art will recognize that the above methods for producing a pinch in a charge sensor are exemplary and not limiting; a pinch may be produced with a number of other methods common in semiconductor manufacturing, e.g., through the use of sacrificial layers, selective deposition and etch, or additional lithographic masks, among others.

The density of an array can be from 2 to as many as a billion or more different reaction sites per square cm. Very high density arrays are useful in the invention including, for example, those having at least about 10,000,000 reaction sites/cm$^2$, including, for example, at least about 100,000,000 reaction sites/cm$^2$, 1,000,000,000 reaction sites/cm$^2$, up to about 2,000,000,000 reaction sites/cm$^2$ or higher. High density arrays can also be used including, for example, those in the range from about 100,000 reaction sites/cm$^2$ to about 10,000,000 reaction sites/cm$^2$. Moderate density arrays useful in the invention can range from about 10,000 reaction sites/cm$^2$ to about 100,000 reaction sites/cm$^2$. Low density arrays are generally less than about 10,000 reaction sites/cm$^2$.

Any of a variety of reaction components can be attached to a charge sensor. For example, a receptor, such as an antibody or lectin; a ligand, such as a nucleotide, epitope, carbohydrate, or drug candidate; a nucleic acid such as target nucleic acid, tether nucleic acid or other nucleic acid set forth in connection with a reaction set forth herein; or an enzyme, such as a polymerase or other nucleic acid binding enzyme, a kinase, phosphatase, exonuclease, protease, or metabolic enzyme. Other useful reaction components include, but are not limited to, components of reactions set forth herein or known in the art of molecular biology or biochemistry.

Multiplex embodiments, including, for example, those that employ an array of charge sensors can be configured such that a single type of reaction component is attached to each charge sensor. For example, the charge sensors in a multiplex embodiment can substantially all be attached to a polymerase. Furthermore, the same species of polymerase can be attached to each of the charge sensor. This configuration can provide an expected uniform output from each charge sensor, but for differences in the other reaction components that come into contact with each respective charge sensor. Such a configuration can be achieved by providing a fluid that is homogeneous with respect to having a single type of polymerase when attaching the polymerases to the charge sensors.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* PolI, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase Family C includes, for example, the *E. coli* DNA Polymerase III alpha subunit Family D includes, for example, polymerases derived from the Euryarchaeota subdomain of Archaea. DNA Polymerases in Family X include, for example, eukaryotic polymerases Pol β, pol σ, Pol λ, and Pol μ, and *S. cerevisiae* Pol4. DNA Polymerases in Family Y include, for example, Pol η, Pol iota, Pol kappa, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein. On the other hand, the large fragment of A-family DNA polymerases, such as Bsu DNA polymerase I (Bsu-LF), naturally lack a 3' to 5' exonuclease function.

Polymerases having 3' to 5' exonuclease activity undergo intramolecular and intermolecular switching as described, for example, in Lamichhane et al. J. Am. Chem. Soc. 135:4735-4742 (2013), which is incorporated herein by reference in its entirety. In some embodiments, it is desirable to use a polymerase that lacks 3' to 5' exonuclease activity. For example, in some embodiments the switching can cause a conformational change that is difficult to distinguish from one or more of the conformational changes that occur due to polymerase activity and that are utilized for sequencing or other analyses. The 3' to 5' exonuclease activity can be removed by removing all or part of the 3' to 5' exonuclease domain or by introducing loss of function mutations into the 3' to 5' exonuclease domain.

The large fragment of A-family DNA polymerases, such as Bsu DNA polymerase I (Bsu-LF), can be further modified for use in a method set forth herein. Native Bsu-LF has no cysteine (Cys) residues. One or more Cys residue can be engineered at a surface accessible location of Bsu-LF to allow for a convenient attachment site for a tether or other linker having a sulfhydryl reactive moiety. Candidate sites for introduction of a Cys mutation can be determined from inspection of crystal structures of Bsu-LF or other homologous A-family polymerases.

Figure 7:
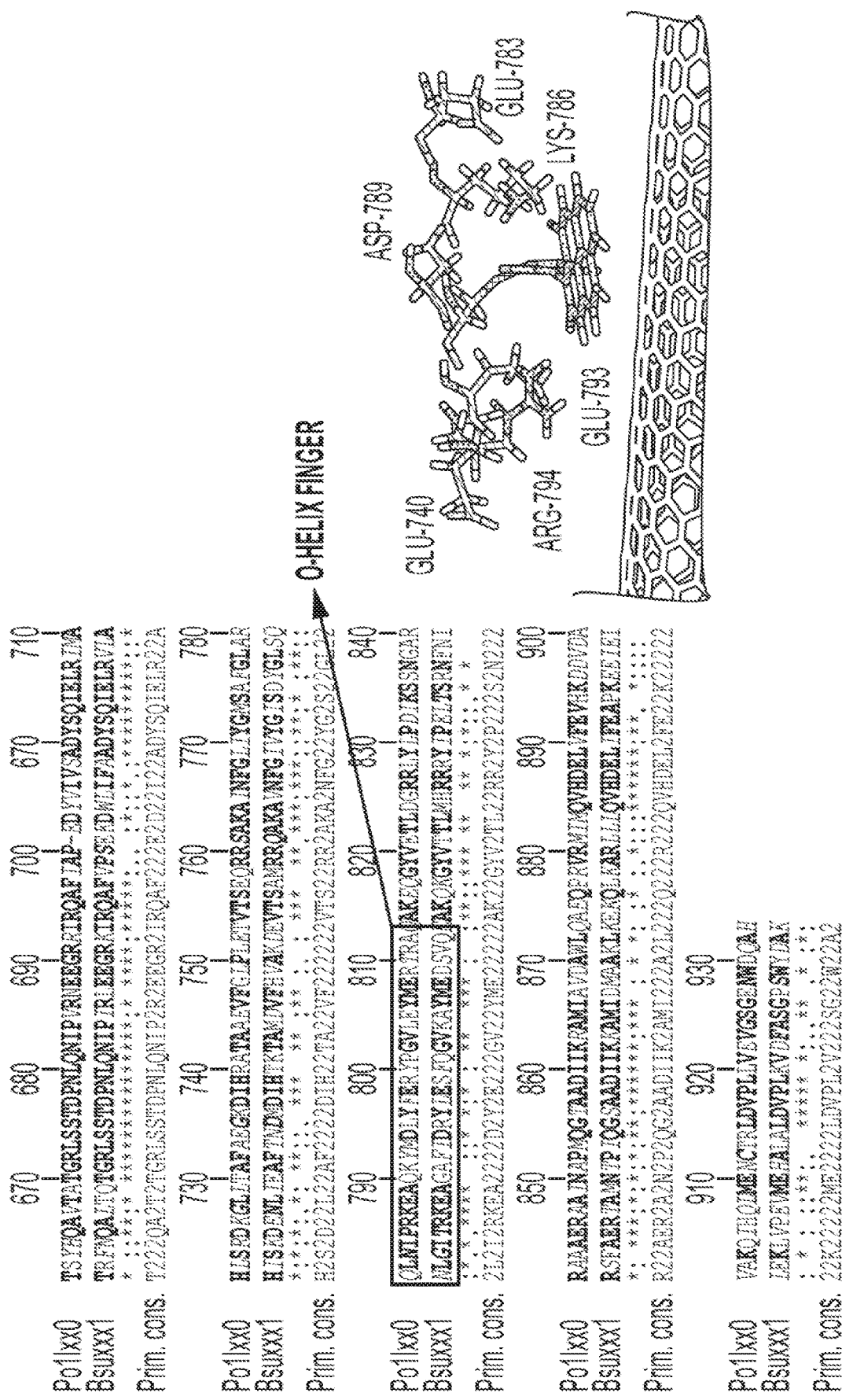
FIG. 7 shows aligned sequences of Klenow fragment (PolIxxo) and Bsu-LF (Bsuxxx1), in which the location of the O-helix finger domain of Klenow fragment and the aligned location in Bsu-LF is boxed. Also shown in the inset at the right is a model showing the three dimensional locations of several residues of the Klenow fragment O-helix finger juxtaposed with a model of a nanotube.

It may also be desirable to engineer Bsu-LF to introduce charged residues that will interact favorably with a charge sensor. For example, a beneficial modification is to introduce one or more residues from the O-helix finger domain of Klenow fragment into comparable position(s) of Bsu-LF, the net result of which is to introduce more charged amino acids into the mutant Bsu-LF. See FIG. 7 for the location of the O-helix finger domain of Klenow fragment (PolIxxo in the figure) and the location to be replaced in Bsu-LF (Bsuxxx1) in the figure. Similar changes can be made to other A-family polymerases such as Taq DNA polymerase or Bst DNA polymerase Polymerases can be characterized according to their processivity. A polymerase can have an average processivity that is at least about 50 nucleotides, 100 nucleotides, 1,000 nucleotides, 10,000 nucleotides, 100,000 nucleotides or more. Alternatively or additionally, the average processivity for a polymerase used as set forth herein can be, for example, at most 1 million nucleotides, 100,000 nucleotides, 10,000 nucleotides, 1,000 nucleotides, 100 nucleotides or 50 nucleotides. Polymerases can also be characterized according to their rate of processivity or nucleotide incorporation. For example, many native polymerases can incorporate nucleotides at a rate of at least 1,000 nucleotides per second. In some embodiments a slower rate may be desired. For example, an appropriate polymerase and reaction conditions can be used to achieve an average rate of at most 500 nucleotides per second, 100 nucleotides per second, 10 nucleotides per second, 1 nucleotide per second, 1 nucleotide per 10 seconds, 1 nucleotide per minute or slower. As set forth in further detail elsewhere herein, nucleotide analogs can be used that have slower or faster rates of incorporation than naturally occurring nucleotides. It will be understood that polymerases from any of a variety of sources can be modified to increase or decrease their average processivity or their average rate of processivity (e.g. average rate of nucleotide incorporation) or both. Accordingly, a desired reaction rate can be achieved using appropriate polymerase(s), nucleotide analog(s), nucleic acid template(s) and other reaction conditions.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. It will be understood that polymerases from any of a variety of sources can be modified to increase or decrease their tolerance to high temperature conditions. A heat spike (i.e. brief time period of increased temperature) can be used to inactivate one or more heat inactivatable polymerases in an array while leaving thermophilic polymerases in an active state for subsequent reactions or for subsequent cycles of a sequencing reaction.

In an alternative embodiment, several different types of reaction component can be attached across the multiplex collection of charge sensors. For example, a first subset of charge sensors in an array can be attached to a first species of polymerase and a second subset of charge sensors in the array can be attached to a second species of polymerase. Two, three, or more species of polymerase can be used. The use of different species of polymerase can be useful when the different polymerases have different specificity or sensitivity for different types of nucleotides or different template sequences. For example, the different types of polymerases can produce mutually distinguishable signals detectable by the charge sensors when incorporating the same type of nucleotide into a nascent strand of a nucleic acid. In another example, the different types of polymerases can include at least one DNA polymerase and at least one RNA polymerase. Such a configuration can be achieved by providing a fluid that is heterogeneous with respect to having multiple type of polymerase when attaching the polymerases to the charge sensors.

In some configurations, a charge sensor will have a capacity to attach more than one reaction component of a particular type. For example, a charge sensor may have a capacity to attach more than one polymerase. Depending on the size of the charge sensor and volume occupied by the polymerase, the charge sensor may have a capacity to attach at least 2, 3, 4, 5, 10, 15, 25 or more polymerases. This can be the case for a plurality of charge sensors in an array. As will be set forth in further detail below, conditions can be temporarily imposed to decrease the capacity of a charge sensor, increase the steric bulk of a polymerase (or other reaction component), or otherwise favor attachment of a single polymerase (or other reaction component) to an individual charge sensor. Again, the conditions can be applied to an array of charge sensors.

A reaction component can be attached to a charge sensor using any of a variety of chemistries known in the art. For example, chemical linkers can be used. In many embodiments, the surface of the charge sensor is one of $SiO_2$, $Al_2O_3$, $HfO_2$, $Ta_2O_5$. Other oxides can also be used, for example from the lanthanide group. Nitrides and oxinytrides are also possible. The attachment to a linker can conveniently be made through a surface hydroxyl. In particular embodiments, the linker molecule includes at least a first and a second functional group. Generally, the first functional group interacts with the charge sensor and the second functional group interacts with the reaction component. Exemplary first functional groups include a pyrene, a benzene, a cyclohexane, and 2,3-dichloro-5,6-dicyano-1,4-benzoquinone. An exemplary second functional group is maleimide. Other chemistries known to covalently link proteins to surfaces or other moieties can be used such as those sold by Thermo Fisher (Waltham, Mass.), or Sigma Aldrich (St. Louis, Mo.). The chemical group on the polymerase attached to the tethers can be thiol, amine or carboxylic group. In certain embodiments in which the conduction channel is a SWNT, the surface of a SWNT is a roughly one atom thick layer of graphite. The linker molecule can be covalently linked to one or few carbon atom, or it can interact with a sidewall of the SWNT through pi-pi stacking.

A reaction component can be attached to a charge sensor by a non-covalent linkage such as one formed between a receptor and a ligand. Particularly useful linkages are those between streptavidin (or variants or analogs thereof) and biotin (or its analogs), those between complementary nucleic acids, those between antibodies and epitopes and the like. Members of the above pairs can be linked to a reaction component and charge sensor, respectively, such that contacting a fluid containing the reaction components with a solid support having the charge sensor will result in formation of the noncovalent bond that tethers the reaction component to the charge sensor.

In some embodiments, the reaction components from the fluid attach to the charge sensors to form a conducting tether. Exemplary conducting tethers include those having a structure that includes doped polythiophene, poly(3,4-ethylenedioxythiophene), polyacetylenes, polypyrroles, polyanilines, polyfluorenes, polyphenylenes, polypyrenes, polyazulenes, polynaphthalenes, polycarbazoles, polyindoles, or polyazepines. Charge doping of these tether structures can be achieved by oxidation of the polymer. Exemplary conducting tethers and methods for their creation are set forth in Vernitskaya et al. Russ. Chem. Rev. 66:443ff (1997); MacDiarmid, Angew. Chem., Int. Ed. 40:2581-2590 (2001); or McNeill et al., Aust. J. Chem. 16:1056-75 (1963), each of which is incorporated herein by reference in its entirety.

In particular embodiments, a solid support can be within or part of a vessel such as a well, tube, channel, cuvette, Petri plate, bottle or the like. A particularly useful vessel is a flow-cell, for example, as described in US 2010/0111768 A1 or Bentley et al., Nature 456:53-59 (2008), each of which is incorporated herein by reference in its entirety. Exemplary flow-cells are those that are commercially available from Illumina, Inc. (San Diego, Calif.). Flow cells are convenient for delivering bulk reagents to an array of charge sensors during attachment of reaction components to the charge sensors or during subsequent reactions carried out with the reaction components on the charge sensors. Cyclic processes such as nucleic acid sequencing reactions are particularly well suited for flow cell devices. Another particularly useful vessel is a well in a multiwell plate or microtiter plate.

A method set forth herein can include steps of contacting a plurality of charge sensors with a fluid containing a plurality of reaction components of a particular type under conditions wherein the reaction components are in fluid communication with the plurality of charge sensors and the reaction components attach to the charge sensors. The result can be that each of the charge sensors becomes attached to a single one of the reaction component even when number of reaction components in the fluid is greater than the number of charge sensors that are contacted by the fluid. The fraction of the charge sensors that attach to one and only one of the reaction components of the particular type would be expected to conform to the Poisson distribution. The Poisson distribution sets a maximum of 37% occupancy for the fraction of charge sensors that would attach to only a single reaction component of a particular type when those reaction components were delivered to the charge sensors in a bulk fluid. However, in accordance with the methods set forth herein, bulk fluid delivery of reaction components of a particular type (e.g. polymerase or other nucleic acid enzyme) can result in greater than 35%, 40%, 50%, 75%, 90%, 95% or 99% of the charge sensors in the plurality being occupied by a single reaction component of the particular type.

In some embodiments of the methods, reaction components can be transported from bulk solution to charge sensors, for example, by diffusion or other passive process. Attachment of the reaction components to the charge sensors can thus occur, for example, in accordance with chemistries set forth herein or known in the art. Alternatively, reaction components can be actively transported to the charge sensors, for example, via electric field (e-field) assisted transport. Again, attachment of the reaction components to the charge sensor can result using chemistries set forth herein or known in the art.

A method set forth herein can be modified to use electric field (e-field) assisted transport of reaction components to sites that contain charge sensors. For example, each charge sensor on a solid support can be present at a site that is electrically coupled to a power source to produce an electric charge that attracts polymerases or other reaction components to that site and into proximity with the charge sensor at that site. Exemplary methods and apparatus for using e-field assist to attract analytes to sites of an array are described in US 2009/0032401 A1, which is incorporated herein by reference in its entirety. E-field assist can be used in a method of the present disclosure, for example, under conditions where a plurality of different polymerases (or other reaction components) is in solution such that the polymerases are in fluidic communication with the plurality of charge sensors. The charge at the site of each charge sensor can be adjusted to achieve a desired rate or amount of transport for the polymerase (or any other particular type of reaction component).

In particular embodiments that utilize e-field assisted transport, the e-field can be consistently applied throughout the course of the reaction that is used to attach a polymerase (or any other particular type of reaction component) to a charge sensor. Alternatively, the e-field can be changed (e.g. increased or decreased) as the attachment reaction progresses and charge sensors fill with polymerase (or any other particular type of reaction component). For example, increasing the e-field can provide the benefit of increasing the number of charge sensors that attach to a polymerase. The rate at which the e-field is increased, and the amplitude range for the increase, can be selected to balance the increasing rate of reaction component transport to charge sensors over time with the increasing number of charge sensors that have become attached to polymerase over that same period of time. The rate of change for the e-field can be based on a predicted or expected rate of polymer attachment. Alternatively, the e-field can be changed in response to empirical detection of polymerase attachment to the charge sensors as set forth in further detail herein.

In particular embodiments, an e-field can be applied substantially uniformly to all of the sites of an array that have charge sensors. Thus, polymerases (or other reaction components) that are in solution will have an equal probability of being transported to any given charge sensor. In an alternative embodiment, an e-field can be applied to only a subset of the charge sensor sites that are present in an array. In this way, e-field assist can be used to selectively attach polymerase (or other reaction component) to some charge sensors over others. Furthermore, if desired, an attractive charge can be applied at a first subset of charge sensor sites in order to transport polymerase to the first subset of sites and in the meantime a repellant charge can be applied to a second subset of charge sensor sites to inhibit polymerases from being transported to those sites or to remove (e.g. via desorption or degradation) polymerase from the second subset of sites. Similarly a repellant charge can be applied to interstitial regions of an array that do not contain charge sensors in order to inhibit polymerases from being transported to the interstitial regions or to remove (e.g. via desorption or degradation) polymerases from the interstitial regions.

In many configurations an amplifier that is used for a charge sensor will occupy substantially more space than the sensor itself. For example, readout circuitry may occupy an area of a detection device that is anywhere from 2×2 microns to 20×20 microns, whereas a single nanowire transistor may occupy as little as 100×500 nanometers. The size and dimensions of an array of charge sensors can in some embodiments be limited by the space occupied by multiple amplifiers, for example, if an amplifier is present for each charge sensor. The limitation can be overcome in particular embodiments of the present apparatus and methods by configuring an array of charge sensors such that a each amplifier is operationally connected to several charge sensors. For example, 2, 3, 4, 5, 6, 8, 10 or more charge sensors can be connected to the same amplifier. Thus a higher density of charge sensors can be present on an array than in a configuration where there is a one to one connectivity between amplifiers and charge sensors. In operation, an amplifier can be assigned to amplify signal from only one of many charge sensors to which it is (or was at one time) connected. For example, the array of charge sensors can be loaded by contacting it with a fluid containing a plurality of reaction components of a particular type. This loading technique may result in a substantial number of the charge sensors being attached to more than one reaction component of a particular type and others not being loaded with any of that type of reaction component at all. Among several charge sensors that are connected to a common amplifier, a single sensor that has attached to only a single reaction component can be distinguished from the others that are overloaded or unloaded and the amplifier can be assigned to acquire signal from the single loaded charge sensors while not acquiring signal from the other charge sensors to which it is (or was) connected.

In some embodiments, an individual charge sensor will have capacity for greater than one reaction component of a particular type. Taking a polymerase as an example, each charge sensor may have capacity to attach several polymerase molecules at once. In such cases, the polymerase can be attached to a repellant moiety that occupies a volume of space that sterically hinders more than one of the polymerases that is bound to another repellant moiety from attaching to an individual charge sensor. Similarly, the repellant moiety can have a charge polarity that electrostatically hinders more than one of the polymerases that is bound to another repellant moiety from attaching to the same charge sensor.

A particularly useful repellant moiety is nucleic acid. A repellant nucleic acid can provide both steric and electrostatic hindrance to limit occupancy. A repellant nucleic acid is well suited to polymerases, nucleic acid enzymes and other reaction components that have a binding affinity for nucleic acids. However, it will be understood that this type of affinity is not necessary because synthetic methods can be used to attach repellant nucleic acids to reaction components, for example, using the linkers, tethers and attachment chemistries set forth herein or known in the art. The length, sequence composition, or secondary structure of the repellant nucleic acid can be modulated to achieve a desired occupancy. For example, larger nucleic acids can be used when the charge sensors have a relatively high capacity for the reaction component to which the charge sensor will be attached. Smaller nucleic acids can be sufficient for limiting loading of smaller charge sensors (or when relatively large reaction components or highly charged reaction components are used thus requiring only a small increase in repellant properties). Nucleic acids are also useful as repellant moieties since the sequence of the nucleic acid can be selected to achieve desired binding properties to a polymerase or other nucleic acid enzyme.

In some embodiments, a repellant nucleic acid can be compacted into a nanoball structure. Methods of compacting nucleic acids are known in the art (for example, as described by Bloomfield, Curr. Opin. Struct. Biol. 6(3): 334-41 (1996), and US Pat. App. Pub. No. 2007/0099208 A1, each of which is incorporated herein by reference in its entirety). For example, an alcohol or polyamine such as spermine or spermidine can be used. A compacted nucleic acid will have a structure that is more densely packed than the structure of the nucleic acid in the absence of a compacting agent or compacting condition and the structure will typically resemble a ball or globule. The generation of such compacted nucleic acid balls is useful for creating repellant moieties. Various methods can be used to generate balls of a desired size, for example, using various compacting techniques and/or varying the number of copies in an amplicon. Generally, the compacted amplicons have an average diameter or width ranging from about 0.1 µm to about 5 µm, for example, about 0.1 µm, about 0.2 µm, about 0.5 µm, about 1 µm, 2 µm, about 3 µm, about 4 µm and about 5 µm.

Other polymeric molecules are also useful as repellant moieties, including without limitation, polyethylene glycol, polythenes, polypropylene, polyvinyl chloride, Teflon, nylon, polyamides, polyacetals, polyesters, Buna rubbers, polyacrylates, polystyrene, and polychlorotrifluoroethene. Beads or particles made of solid support materials or gels can also function as repellant moieties.

A repellant moiety can remain attached to a reaction component while the reaction component participates in a particular reaction that is to be detected by a charge sensor to which the reaction component is attached. For example, a repellant moiety that is bound to a polymerase while the polymerase is loaded onto and attached to a charge sensor can remain attached to the polymerase in a subsequent nucleotide addition reaction that is detected by the charge sensor. Alternatively, the repellant moiety can be removed from the reaction component after the reaction component has been attached to a charge sensor. Taking again the example of a polymerase, a repellant moiety such as repellant nucleic acid can be removed from the polymerase prior to the polymerase participating in a detected reaction with a target nucleic acid. Repellant moieties that are bound to a polymerase or other reaction component can be removed by techniques known to those skilled in the art to result in removal. For example, non-covalently bound moieties can be removed by washing, or competitive displacement using other moieties that bind to the reaction component. Covalently bound moieties can be removed by chemical or physical means such as those set forth herein in regard to cleaving tethers. Repellant moieties once removed from a reaction component can be washed away from the charge sensor to which the reaction component remains attached.

In some embodiments, a charge sensor that has a capacity for more than one reaction component of a particular type, can be overloaded such that an individual charge sensor is attached to several of the reaction components and then reaction components can be removed (or inactivated or degraded) from the charge sensor leaving only a single active reaction component attached to the individual charge sensor. For example, a method of attaching reaction components to charge sensors can be carried out to create cleavable tethers between each reaction component and the charge sensor to which it is attached. In some cases the reaction components that are delivered in a fluid can include precursors to cleavable tethers, the charge sensors can include precursors to cleavable tethers or both the reaction component and charge sensor can have precursors that react together to form a cleavable tether.

Cleavable tethers can be cleaved by bond breakage due to physical or chemical processes. For example, a method set forth herein can include a step of cleaving a cleavable tether by photochemical cleavage, electrochemical cleavage, electric field, mechanical agitation, chemical cleavage or heat. Useful cleavable tethers and their precursors include those used for modification of proteins and are commercially available, for example, from Thermo Fisher (Waltham, Mass.), or Sigma Aldrich (St. Louis, Mo.).

Other methods can be used to remove one or more reaction components from a charge sensor. For example, removal can be achieved by degrading one or more reaction components from each charge sensor. Degradation can be achieved by physical methods such as heat, photo-oxidation, sonication or the like. Chemical degradation is also possible for example using pH changes, chemical denaturants, proteases or the like. In some cases, the extent of degradation can be modulated by contacting the sensor-attached reaction components with a protection moiety. The amount of protection moiety supplied to an array of charge sensors can be titrated to result in binding to a single reaction component, on average, per charge sensor. When degradation is subsequently carried out all but the protected reaction component attached to each charge sensor will be degraded. This will leave a single reaction component attached to each charge sensor. The protection moiety can remain bound to the reaction component as it participates in a reaction that is detected by the charge sensor, or the protection moiety can be removed. In some cases, the degradation can happen by binding the polymerase active site with a chemically or photochemically active oligonucleotide analog. A chemical or photochemical treatment can be applied to crosslink the oligonucleotide analog to the polymerase. As a result, these polymerase can be rendered incapable of accepting a target nucleic acid, or primer, or the polymerase may be rendered incapable of conformational changes (e.g. open-close conformation changes) that would have been detected by charge sensor.

An example of a useful protection moiety is a nucleic acid such as a DNA nanoball. For example, a nucleic acid can be used to bind to a polymerase or other nucleic acid enzyme to provide stability against denaturation or chemical modification. A nucleic acid can also provide a steric block preventing proteases from having access to a polymerase that is attached to a charge sensor. Another example is a primer hybridized single stranded DNA; in this case the 3' end of the primer will be bound to the catalytic center of the polymerase, preventing binding of reactive polymerase deactivation moieties. A further example of a protection moiety is a protein such as an antibody that specifically targets a polymerase. The protein or antibody can protect against chemical modification or provide a steric block preventing proteases from having access to the polymerase. If it is desirable to remove the antibody, the antibody could be removed using, for example, heat. An appropriate temperature would be one at which the antibody is no longer stably bound to the polymerase, but at which the polymerase is stable. Other materials that have been exemplified herein for use as repellant moieties can serve as protection moieties.

Degradation, inactivation or removal of excess reaction components from charge sensors can be carried out with or without monitoring of the charge sensors to determine the extent of degradation or removal. For example, in particular embodiments a process of removing one or more reaction components of a particular type from modified charge sensors can include steps of (i) removing one or more of the reaction components from each of the modified charge sensors, (ii) monitoring the charge sensors to distinguish the presence of multiple reaction components from the presence of a single reaction component, and (iii) discontinuing the removing to leave a single one of the reaction components attached to each of the modified charge sensors. The status of the charge sensor can be monitored by detecting changes in signal from the charge sensor. Alternatively or additionally, a different sensor can be used to detect presence or absence of reaction components at the surface of the charge sensor. Any of a variety of detection modalities can be used including for example, fluorometry to detect fluorescent labels on reaction components, optical scatter methods, absorbance methods to detect chromophores and other analytical detection methods known in the art pertaining to the detection of proteins and other reaction components.

A method of the present disclosure can include a step of providing one or more target nucleic acids to a solid support that comprises at least one charge sensor. In particular embodiments the charge sensor will have been previously attached to another reaction component that will react with the nucleic acid(s) in a desired reaction, examples of which include nucleic acid enzymes such as polymerases. In other embodiments target nucleic acid(s) can be delivered to a charge sensor before or at the same time that other reaction components (e.g. nucleic acid enzymes or polymerases) are delivered to the charge sensor(s).

Target nucleic acids used in a method or apparatus of the present disclosure can be composed of DNA, RNA or analogs thereof. The source of the target nucleic acids can be genomic DNA, messenger RNA, or other nucleic acids from native sources. In some cases the target nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of target nucleic acids prior to use in a method or apparatus set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof.

Exemplary biological samples from which target nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli, Staphylococci* or *Mycoplasma pneumoniae*; an archae; a virus such as Hepatitis C virus, ebola virus or human immunodeficiency virus; or a viroid. Target nucleic acids can be derived from a homogeneous culture or population of the above organisms or alternatively from a collection of several different organisms, for example, in a community or ecosystem.

Target nucleic acids need not be derived from natural sources and can instead be synthesized using known techniques. For example, gene expression probes or genotyping probes can be synthesized and used in the methods and apparatus set forth herein.

In some embodiments, target nucleic acids can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid. For example, PCR amplification produces fragments having a size defined by the length of the nucleotide sequence on the original template that is between the locations where flanking primers hybridize during amplification.

A population of target nucleic acids, or amplicons thereof, can have an average strand length that is desired or appropriate for a particular application of the methods or apparatus set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of target nucleic acids, or amplicons thereof, can be in a range between a maximum and minimum value set forth above.

In some cases a population of target nucleic acids can be produced under conditions or otherwise configured to have a maximum length for its members. For example, the maximum length for the members that are used in one or more steps of a method set forth herein or that are present in a particular composition can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of target nucleic acids, or amplicons thereof, can be produced under conditions or otherwise configured to have a minimum length for its members. For example, the minimum length for the members that are used in one or more steps of a method set forth herein or that are present in a particular composition can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for target nucleic acids in a population can be in a range between a maximum and minimum value set forth above.

The present disclosure provides a method of detecting a nucleotide. The method can include the steps of (a) providing a nucleotide binding protein (e.g. a polymerase) tethered to a solid support charge sensor; (b) providing one or more labeled nucleotides, whereby the presence of the label can be detected by the charge sensor when the label is in proximity to the charge sensor; and (c) detecting binding of the labeled nucleotide to the protein using the charge sensor.

The binding of a nucleotide to a nucleic acid binding enzyme, such as a polymerase, can be detected based on the recruitment of a charge label to the enzyme which in turn causes a detectable perturbation in the field around the charge sensor to which the enzyme is attached. Exemplary charge labels are set forth previously herein. In particular embodiments, the charge label is attached to the β- or γ-phosphate position of the nucleotide. An advantage of attaching the label at the beta- or gamma-phosphate position of the nucleotide is that the label can be removed by the catalytic activity of polymerase when incorporating the nucleotide into a nascent strand. However, the label need not be removed by polymerase activity. Thus, the label can be attached at any of a variety of positions on a nucleotide including for example via a linker to the base moiety of a nucleotide (see, for example, the nucleotide positions and linkers set forth in U.S. Pat. Nos. 7,427,673; 7,414,116; and 7,057,026 and PCT publications WO 91/06678 and WO 07/123744, each of which is incorporated herein by reference in its entirety). A label can also be attached at the alpha-phosphate position of the nucleotide or at the ribose moiety of the nucleotide. A label attached to any of a variety of moieties of a nucleotide can optionally be cleaved from the nucleotide after being detected, for example, via cleavage of a charge linker.

A label used in a method or apparatus set forth herein can further include an oligonucleotide moiety. Exemplary oligonucleotide moieties include DNA, RNA, and PNA as set forth previously herein. As exemplified previously herein, an oligonucleotide moiety can be useful for hybridizing to a nucleic acid tether or other nucleic acid so as to localize electric field perturbation to occur with a desired distance of a charge sensor. The oligonucleotide moiety can occur as an intermediary structure between the nucleotide and a charged moiety. However, the charge moiety is optional and need not be located at an end of the oligonucleotide moiety that is distal to the point of attachment to the nucleotide. Although several embodiments are exemplified herein with reference to nucleotide analogs having oligonucleotide moieties that interact with nucleic acid tethers, it will be understood that nucleotide analogs can have other linker components in place of the oligonucleotide moieties. The linker components can comprise one member of a binding pair that interacts with another member that is part of a tether.

In some embodiments, different nucleotide types can be attached to different labels. Thus, the differences in signal arising from the labels can be used to distinguish different nucleotide types. This can be particularly useful for nucleic acid sequencing methods where several different types of nucleotides are delivered to a polymerase in a way that the several different types of nucleotides are present in parallel during a detection event. For example, four different nucleotides having four different charge moieties can be used as exemplified previously herein with regard to FIG. 2 and FIG. 3. Alternatively or additionally, the label moieties can contain oligonucleotide moieties that hybridize to different tether sequences to produce mutually distinct signals at a charge sensor. In some embodiments several labeled nucleotides used in a method set forth herein will have different charge labels, respectively, but each of said labeled nucleotides will have an oligonucleotide moiety that is capable of hybridizing to the same immobilized tether sequence. As set forth previously herein, different nucleotide analogs can have oligonucleotide moieties with different lengths, or alternatively, two or more of the nucleotide analogs can have oligonucleotide moieties that are the same length.

Different nucleotides need not have different labels. The different nucleotides can be delivered to a reaction separately such that the nucleotides are distinguished based on knowledge of when and where they are delivered. For example, a sequencing reaction can include sequential additions of four separate nucleotides per cycle with washes between nucleotide additions. This separate delivery of nucleotides can be done whether the different nucleotides are uniquely labeled or uniformly labeled.

In particular embodiments, a method of nucleic acid sequencing can be performed by (a) providing a polymerase tethered to a solid support charge sensor; (b) providing one or more labeled nucleotides, whereby the presence of the label can be detected by the charge sensor when the label is in proximity to the charge sensor; and (c) detecting incorporation of the labeled nucleotide into a nascent strand complementary to a template nucleic acid using the charge sensor. A plurality of incorporation events can be detected in succession to determine the sequence. Alternatively, only a single incorporation event is detected for each nascent strand and this information is combined with knowledge of the sequence for the nascent strand (or the template to which it is hybridized) to arrive at the sequence.

In multiplex embodiments, the solid support may include a plurality of charge sensors that are tethered to polymerases, and the method includes a step of detecting incorporation of a labeled nucleotide into a nascent strand complementary to a template nucleic acid at each polymerase in the plurality of polymerases. The plurality of polymerases used in a multiplex embodiment can optionally include at least two different types of polymerases. The different types of polymerases can be selected to produce mutually distinguishable signals detectable by the charge sensors when incorporating the same type of nucleotide into a nascent strand of nucleic acid. In this way, an array of charge sensors having different attached polymerases (e.g. one per charge sensor) can distinguish a greater variety of nucleic acid sequences or provide greater sensitivity than would be available using an array having only one type of polymerase attached to the charge sensors. For example, the same template when sequenced by the action of two different polymerases will produce two different series of signals. The two series of signals can be compared or otherwise used in combination to provide a more accurate nucleotide sequence than would be derivable from only one series of signals from only one type of polymerase.

An array of the present disclosure, for example, having been produced by a method set forth herein, can be used for any of a variety of applications. A particularly useful application is nucleic acid sequencing. One example is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, nucleotides are added to a primer (thereby extending the primer) in a template dependent fashion such that detection of the order and type of nucleotides added to the primer can be used to determine the sequence of the template. A plurality of different templates at different charge sensors of an array set forth herein can be subjected to an SBS technique under conditions where events occurring for different templates can be distinguished due to their location at a specific charge sensor of the array.

Flow cells provide a convenient format for housing an array that is produced by the methods of the present disclosure and that is subjected to an SBS or other detection technique that involves repeated delivery of reagents in cycles. For example, to initiate a first SBS cycle, one or more nucleotides (optionally having charge labels), can be flowed into/through a flow cell that houses an array of charge sensors each having an attached polymerase to which a nucleic acid template is bound. Those sites of an array where primer extension causes a nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures and fluidic systems that can be readily adapted for use with an array produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

Sequencing-by-ligation reactions are also useful including, for example, those described in Shendure et al. Science 309:1728-1732 (2005); U.S. Pat. Nos. 5,599,675; and 5,750,341, each of which is incorporated herein by reference in its entirety. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety. In both Sequencing-by-ligation and sequencing-by-hybridization procedures, target nucleic acids (or amplicons thereof) are subjected to repeated cycles of oligonucleotide delivery and detection. Such methods can be readily modified to detect ligase conformational changes or to detect charge labeled oligonucleotides in place of the fluorescent detection of optical labels described in the published methods.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above except that fluorescence detection of optically labeled nucleotides can be replaced with the charge-based detection methods set forth herein. Gene expression can also be detected or quantified using hybridization techniques carried out by direct hybridization to an array or using a multiplex assay, the products of which are detected on an array. Exemplary molecular biological assays that can be used for array-based expression and genotyping analysis are described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety. These methods can be readily adapted by replacing optical labels and fluorescence detection with the charge-based detection techniques, and optionally the charge labels, set forth herein.

A method of nucleic acid sequencing provided by the present disclosure can include the steps of (a) providing a polymerase tethered to a solid support charge sensor; (b) providing one or more labeled nucleotides, whereby the presence of the label can be detected by the charge sensor when the label is in proximity to the charge sensor, wherein the one or more labeled nucleotides have reversible terminator moieties; (c) detecting incorporation of the one or more labeled nucleotides into a nascent strand complementary to a template nucleic acid using the charge sensor, thereby forming a reversibly terminated nascent strand; (d) modifying the reversible terminated nascent strand to render the nascent strand capable of further incorporation of nucleotide; and (e) repeating (b) through (d) to obtain a sequence of the template nucleic acid.

The use of reversibly terminated nucleotides in a sequencing reaction provides advantages of step control to the polymerase extension process that would otherwise be continuous. This step control can be useful for increasing the amount of time that a newly extended nucleic acid strand spends in a detectable state. For example, a charge label that is on a reversibly terminated nucleotide can be maintained on a nascent strand after being added by a polymerase and until a desired amount of signal is accumulated by the charge sensor. This can allow for increased signal collection. Then the sequencing process can proceed by addition of deblocking agent followed by subsequent cycles of nucleotide addition.

Another advantage of the step control conferred by the use of reversibly terminated nucleotides is the ability to synchronize an ensemble of reaction components that undergo the same reaction. Thus, a sequencing method set forth herein can be carried out for multiple copies of the same nucleic acid bound to multiple polymerases at the site where a charge sensor is located (e.g. the multiple polymerases can be attached to a single charge sensor). The detection step used to identify the nucleotide added during each cycle of polymerase activity can be effectively synchronized by use of reversibly terminated nucleotides. Although reversibly terminated nucleotides provide advantages for ensemble detection, it will be understood that sequencing methods employing reversibly terminated nucleotides can be used when a single polymerase is attached to an individual charge sensor.

An ensemble of sequencing reactions can be set up to include a plurality of polymerases attached to a common charge sensor, wherein the polymerases are bound to target nucleic acids having the same template sequence and a primer (or nascent strand) with the same sequence. The polymerases can be attached to the charge sensor as set forth previously herein. Then one or more target nucleic acids comprising multiple repeats of the same template sequence can be contacted with the polymerases. For example, a target nucleic acid molecule having concatameric repeats of the template sequence can be delivered to the polymerases at the particular site. In this case, the subunit of sequence that forms each repeat can function as an individual template sequence. Optionally, the nucleic acid encoding the concatameric repeat can be cleaved to form individual molecules each having a single template sequence. These individual molecules can then be sequenced by polymerases at the site. The nucleic acid encoding the concatameric repeat can be created by rolling circle amplification (RCA), for example, as described in Lizardi et al., Nat. Genet. 19:225-232 (1998) and US Pat App. Pub. No. 2007/0099208 A1, each of which is incorporated herein by reference in its entirety.

Also provided is a method of nucleic acid sequencing that includes the steps of (a) providing a polymerase tethered to a solid support charge sensor; (b) contacting the polymerase with a template nucleic acid and one or more different nucleotide types under conditions wherein the polymerase catalyzes addition of the one or more nucleotide types to form a nucleic acid complement of the nucleic acid template, and wherein the addition of one or more different nucleotide types produces a conformational signal change from the polymerase that is detected by the charge sensor; (c) detecting a change in the signal from the polymerase using the charge sensor; and (d) determining the rate, polarity, amplitude or time duration for the change in the signal for the addition of the one or more different nucleotide type, thereby determining a sequence of nucleotides for the template nucleic acid.

In particular embodiments, a sequence of nucleotides for a nucleic acid template can be determined based on conformational changes occurring in a nucleic acid enzyme such as a polymerase. Distinguishing the conformational changes that occur for each type of nucleotide that the enzyme interacts with and determining the sequence of those changes can be used to determine the sequence of the nucleic acid. For example, a polymerase that sequentially adds of nucleotides to a nascent nucleic acid strand undergoes conformational changes with each nucleotide addition. As set forth in further detail herein, the conformational changes that occur for each type of nucleotide that is added can be distinguished using a charge sensor (or based on knowledge of which nucleotide(s) is/are fluidically delivered to the substrate where sequencing is being monitored) and the sequence of those changes can be detected to determine the sequence of the nucleic acid.

A nucleic acid enzyme can be labeled to produce one or more signals indicative of a conformational change in the enzyme as it interacts with one or more reactants such as a nucleic acid or nucleotide. A polymerase can be conformationally labeled such that activity of the polymerase can be monitored by detection of allosteric charge movement. For example, a polymerase can be conformationally labeled to allow detection of a signal indicative of nucleotide binding, a signal indicative of addition of a nucleotide to a growing nucleic acid molecule, or a signal indicative of an intermediate change in the conformation of the polymerase between binding and catalysis. Accordingly, a polymerase can include at least one non-natural label moiety that is detected by the charge sensor. Polymerase can be engineered to have negative and positive charges that maximize the charge change per unit volume through allosteric movements. If this unit volume is close to the charge sensor, this movement can easily be detected. In particular embodiments, a signal detected by a charge sensor from a conformationally labeled polymerase can distinguish a binding event from a catalytic event. However, such a distinction may not be necessary for some embodiments and the signal can be merely indicative of the overall addition of a nucleotide. Alternatively or additionally, the signal can distinguish binding of a correctly base-paired nucleotide from binding of an incorrectly base-paired nucleotide.

A particularly useful label moiety that can be attached to a polymerase or other nucleic acid enzyme used in a method or apparatus set forth herein is a negative charge label, examples of which include, but are not limited to, a phosphate group, carboxyl group, amino acid, DMT and/or FMOC. Also useful are positive charge labels including, for example, a primary amine Intrinsic labels such as amino acid side chains or naturally occurring post translational modifications (e.g. phosphorylation, addition of flavin, reduction of disulfides or the like) can also provide useful moieties for detection in a method or apparatus set forth herein.

Some embodiments can employ a nucleotide analog that is incorporated into a polynucleotide strand by a polymerase at a rate that is measurably different than the rate at which another nucleotide is incorporated into the strand by the polymerase. Another useful nucleotide analog is one that is bound to a polymerase at a rate that is measurably different than the rate at which another nucleotide is bound to the polymerase. A nucleotide analog that causes a conformational change of a polymerase at a rate that is measurably different than another nucleotide is also useful. The relative rate of binding, incorporation or polymerase conformational change for a nucleotide analog can be measured relative to a natural nucleotide having the same Watson-Crick base pairing partner or relative to other nucleotides that are used in a nucleic acid synthesis reaction. The relative rate can be faster or slower for the nucleotide analog.

According to particular embodiments, a polymerase or other nucleic acid enzyme can be conformationally labeled. Conformational labeling of nucleic acid enzymes provides advantages for nucleic acid sequence analysis. Conformationally labeled molecules, and methods for making and using them, will be exemplified below with regard to labeled polymerases. It will be understood that other nucleic acid enzymes such as exonucleases and reverse transcriptases can be made and used similarly.

Polymerases undergo conformational changes in the course of synthesizing a nucleic acid polymer. For example, polymerases undergo a conformational change from an open conformation to a closed conformation upon binding of a nucleotide. Thus, a polymerase that is bound to a nucleic acid template and growing primer is in what is referred to in the art as an "open" conformation. A polymerase that is bound to a nucleic acid template, primer and a correctly base paired nucleotide is in what is referred to in the art as a "closed" conformation. At a more detailed structural level, the transition from the open to closed conformation is characterized by relative movement within the polymerase resulting in the "thumb" domain and "fingers" domain being closer to each other. In the open conformation the thumb domain is further from the fingers domain, akin to the opening and closing of the palm of a hand. In various polymerases, the distance between the tip of the finger and the thumb can change up to 30 angstroms between the "open" and "closed" conformations. The distance between the tip of the finger and the rest of the protein domains can also change up to 10 angstroms. It will be understood that larger changes may also occur and can be exploited in a method set forth herein such that a change that is greater than 10 angstroms can be detected. Furthermore, smaller changes can be detected including those that are less than about 10, 8, 6, 4, or 2 angstroms so long as the change in distance is sufficient to be detectable using a charge sensor.

In particular embodiments, a charge label that is attached to a finger domain can be attached to a residue at position 376 or residues within 5 angstroms radius from position 376 of the Phi29 DNA polymerase and a label that is attached to the thumb or other domain can be attached to a residue at position 535, 203, 510, 564, or residues within 5 angstroms radius from these positions of the Phi29 DNA polymerase. Labels can be attached at positions and using methods set forth in US Pat. App. Pub. No. 2011/0312529 A1; U.S. Pat. No. 6,908,763 or WO 2010/068884 A2, each of which is incorporated herein by reference in its entirety.

A change in conformation of a polymerase, for example, from an open conformation to a closed conformation, can be detected using a conformational label. Any label can be used that produces a charge signal that is responsive to a change in the structure, shape or arrangement of amino acid residues such as the changes that occur between the open and closed conformations of a polymerase.

A charge label can be attached to a polymerase, for example, via covalent linkage. Alternatively or additionally, a probe can be attached to another molecule that is in proximity to a polymerase, such that a conformational change in the polymerase causes a change in signal from the probe. For example, the polymerase can be attached to a charge sensor and the charge sensor can have a probe that is capable of interacting with the polymerase in a way that signals from the probe change in response to conformational changes of the polymerase. In a particular embodiment, a charge label can be attached site specifically to a polymerase by introducing cysteine residue at a desired location in the polymerase and then modifying the polymerase with a label having a moiety that reacts specifically with the sulfur group of cysteine, an exemplary reactive moiety being a reactive maleimide moiety. Labels can also be introduced to a polymerase or other nucleic acid enzyme by split inteins as described in Yang et al. J. Am. Chem. Soc., 131:11644-11645 (2009), which is incorporated herein by reference in its entirety. Labels can also be introduced to nucleic acid enzymes by genetically encoded unnatural amino acids. One example is described in Fleissner et al. Proc. Nat'l. Acad. Sci. USA 106:21637-42 (2009), which is incorporated herein by reference in its entirety.

In some embodiments, one or more tethers can be attached to a polymerase at locations on the polymerase where conformational changes are transmitted to a charge sensor to which the tethers are also attached. For example, conformational changes can cause a perturbation that is transmitted by one or more conducting tethers to a charge sensor. In some cases a single polymerase can be attached to a charge sensor via two or more tethers. In this configuration, changes in the conformation of the polymerase can alter the relative positions of the two or more tethers, which can in turn produce field perturbations that can be detected by the charge sensor. One or more tethers can be site selectively attached to a polymerase using known methods of mutagenesis, chemical modification, or both. For example, one or more cysteine can be introduced as site specific mutation(s) in an engineered polymerase allowing attachment of a sulfur reactive tether to the cysteine(s). Exemplary attachment points include those set forth herein and in US Pat. App. Pub. No. 2011/0312529 A1 (which is incorporated herein by reference in its entirety) for attachment of conformational labels.

In addition to the conformational changes set forth herein and otherwise known in the art, polymerases undergo several transitions in the course of adding a nucleotide to a nascent strand. The transitions can be distinguished from each other, for example, by kinetic characterization. Distinguishable transitions include, for example, those set forth in US Pat. App. Pub. No. 2011/0312529 A1. One or more of the transitions that a polymerase undergoes when adding a nucleotide to a nucleic acid can be detected by a charge sensor, for example, using a polymerase that is optionally conformationally labeled. Time based or kinetic measurement of signals detected by a charge sensor to which a polymerase is attached can be used to distinguish one transition from another.

In particular embodiments, time-based or kinetic measurements of a polymerase attached to a charge sensor can be used to distinguish the species of nucleotide that is added to a nucleic acid. For example, a time based or kinetic measurement can be used to distinguish the species of nucleotide that is bound to a polymerase to form one or more of the complexes set forth in US Pat. App. Pub. No. 2011/0312529 A1. Alternatively or additionally, time-based or kinetic measurements of a charge sensor-attached polymerase can be used to distinguish the binding and/or incorporation of a correctly Watson-Crick base-paired nucleotide from one that is incorrectly base-paired to the template nucleic acid.

Methods that use time-based or kinetic discrimination of nucleotides, can be facilitated by use of very fast mixing of reagents at the charge sensors coupled with real time detection. The mixing can occur on the sub-milliseconds timescale in accordance with available stopped-flow instrumentation. The fast mixing of reagents can be achieved using fast fluidics, active or passive mixing, and proper confinement (e.g. mix blousing) of the reaction to overcome limitations by diffusion. Stopped-flow delivery is particularly useful. Stopped flow delivery provides delivery of fluid to a detection site using rapid flow of the fluid followed by abrupt stoppage of the flow. The fluid that is delivered typically displaces an equal volume of fluid from the detection site. The fluid can mix with a solid-phase analyte such as a polymerase attached to a charge sensor. The dead time for stopped-flow fluid delivery can be, for example, less than 2 milliseconds (msec). Accordingly, the dead time can be no longer than 2 msec, 1.5 msec, 1 msec, 0.8 msec, 0.6 msec, 0.5 msec or 0.4 msec. For useful stopped flow and rapid mixing fluidic systems see, for example, Chance, B. J. Frank. Inst., 229, 613 (1940), and US Pat. App. Pub. No. US 2013/0165328 A1, each of which is incorporated herein by reference in its entirety.

A sequence of time-based or kinetic measurements for a charge-sensor attached polymerase can be used to determine the sequence of a template nucleic acid being used by the polymerase to synthesize a complementary strand. It will be understood that the sequence of the template strand can be inferred from the sequence of nucleotides incorporated into the strand that is being extended. As such, determination of the sequence of one strand will be understood to include determination of the sequence of its complementary strand.

Any of a variety of nucleotide species can be useful in a method or composition set forth herein. For example, naturally occurring nucleotides can be used such as ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Typically, dNTP nucleotides are incorporated into a DNA strand by DNA polymerases and NTP nucleotides are incorporated into an RNA strand by RNA polymerases. In particular embodiments, NTP nucleotides or analogs thereof can be incorporated into DNA by a DNA polymerase, for example, in cases where the NTP, or analog thereof, is capable of being incorporated into the DNA by the DNA polymerase and where the rate or time duration for a DNA polymerase transition using the NTP, or analog thereof, can be distinguished from the rate or time duration for the DNA polymerase transition using another nucleotide. Alternatively, dNTP nucleotides or analogs thereof can be incorporated into RNA by an RNA polymerase, for example, in cases where the dNTP, or analog thereof, is capable of being incorporated into the RNA by the RNA polymerase and where the rate or time duration for an RNA polymerase transition using the dNTP, or analog thereof, can be distinguished from the rate or time duration for the RNA polymerase transition using another nucleotide. Additionally, dNTP nucleotides or analogs thereof can be incorporated into DNA from an RNA template by a reverse transcriptase, for example, in cases where the dNTP, or analog thereof, is capable of being incorporated into the DNA from an RNA template by a reverse transcriptase and where the rate or time duration for a reverse transcriptase transition using the dNTP, or analog thereof, can be distinguished from the rate or time duration for the reverse transcriptase transition using another nucleotide. The relative difference in rate or time duration can be a relative increase in the rate, a relative increase in duration, a relative decrease in rate or a relative decrease in duration.

Non-natural nucleotide analogs are also useful. Particularly useful non-natural nucleotide analogs include, but are not limited to, those that produce a detectably different rate or time duration for a polymerase transition that can be distinguished from the rate or time duration for a polymerase transition with another nucleotide. For example, a non-natural nucleotide analog may usefully produce a detectably different rate or time duration for a polymerase transition that can be distinguished from the rate or time duration for the same transition of the polymerase with another nucleotide such as a naturally occurring nucleotide. Exemplary nucleotide analogs that can be used include, but are not limited to, dNTPαS; NTPαS; nucleotides having unnatural nucleobases identified in Hwang et al., Nucl. Acids Res. 34:2037-2045 (2006) (incorporated herein by reference in its entirety) as ICS, 3MN, 7AI, BEN, DMS, TM, 2Br, 3Br, 4Br, 2CN, 3CN, 4CN, 2FB, 3FB, MM1, MM2 and MM3; or nucleotides having other non-natural nucleobases such as those described in Patro et al. Biochem. 48:180-189 (2009) (incorporated herein by reference in its entirety) which include 2-amino-1-deazapurine, 1-deazapurine, 2-pyridine, hypoxanthine, purine, 6-Cl-purine, 2-amino-dA, 2-amino purine or 6-Cl-2-amino-purine or nucleotides having non-natural nucleobases such as those described in Krueger et al. Chem Biol. 16:242-8 (2009) (incorporated herein by reference in its entirety) which include iso-G, iso-C, 5SICS, MMO2, Ds, Pa, FI, FB, dZ, DNB, thymine isosteres, 5-NI, dP, azole-carboxamide, xA, Im-No, Im-ON, J, A*, T*.

Non-natural nucleotide analogs having 5' modifications are particularly useful. The non-natural nucleotide analog will typically have a triphosphate but can have more or fewer phosphates. In particular embodiments, one or more of the alpha phosphate, beta phosphate or gamma phosphate of a non-natural nucleotide is covalently attached to a moiety other than oxygen. A moiety that is attached to a phosphate or otherwise present at the 5' position can provide a negative charge, a positive charge, metal-chelating activity or steric bulk. Exemplary moieties include, but are not limited to, amino acids, in the L-enantiomer form or R-enantiomer form, such as histidine, aspartate, glutamate, tryptophan, phenylalanine, methionine, tyrosine, cysteine, glycine alanine, or proline; an amino group; a chelated metal such as magnesium or manganese; a methyl group; a halogen such as bromine, chlorine or iodine; a thiol group; an electron withdrawing group; an electron donating group; an aromatic amine; or an aliphatic amine. These and other moieties may be advantageous in embodiments where they provide an interaction with a polymerase, or other nucleic acid enzyme, that differs from the interaction that the enzyme has with a nucleotide lacking the moiety. As such, the presence and absence of the moiety on respective nucleotide species can be exploited to distinguish the nucleotide species in a sequencing method, for example, based on the rate, time duration and/or intensity for a conformational signal change in a nucleic acid enzyme acting on the nucleotide species.

A reaction composition or method can include one or more nucleotide species. For example, a reaction composition or method used for sequence analysis can include four different nucleotide species capable of forming Watson-Crick base pairs with four respective nucleotide species in a nucleic acid template being synthesized. Particular embodiments can include at least two different nucleotide species, at least three different nucleotide species, at least four different nucleotide species, or more. At least two of the nucleotide species can be non-natural nucleotide analogs, at least three of the nucleotide species can be non-natural nucleotide analogs, or at least four of the nucleotide species can be non-natural nucleotide analogs. Thus a reaction composition or method can include a mixture of natural nucleotides and non-natural nucleotide analogs. Alternatively, a reaction composition can lack natural nucleotides having instead only non-natural nucleotide analogs. The reaction can be carried out under conditions in which only non-natural nucleotide analogs are incorporated into a growing nucleic acid by a polymerase or other nucleic acid enzyme.

In some embodiments, a reaction composition or method can include nucleotide species that base-pair with no more than one nucleotide species in a nucleic acid template. For example, a method can be carried out under conditions wherein different nucleotide species are contacted with a polymerase and nucleic acid in separate, sequential reactions. Specifically, a nucleotide species that base-pairs with A can be added in a first reaction, a nucleotide species that base-pairs with C can be added in a second reaction, a nucleotide species that base-pairs with T can be added in a third reaction, and a nucleotide species that base-pairs with G can be added in a fourth reaction. The reactions are referred to as first, second, third and fourth merely to illustrate that the reactions are separate but this does not necessarily limit the order by which the species can be added in a method set forth herein. Rather, nucleotide species that base-pair with A, C, T or G can be added in any order desired or appropriate for a particular embodiment of the methods. Typically in a sequencing method nucleotide species that base-pair with four different nucleotide species in a given template nucleic acid are added sequentially to complete a cycle of the sequencing method. However, it will be understood that fewer than four nucleotide additions can be used in some embodiments. Furthermore, it will be understood that mixtures of nucleotides that base-pair with more than one but no more than 2, 3 or 4 nucleotide species can be used. Similarly, mixtures of nucleotides that base-pair with more than two but no more than 3 or 4 nucleotide species can be used, or mixtures of nucleotides that base-pair with more than three but no more than 4 nucleotide species can be used.

Multiplex methods are also possible. For example, a solid support used in a method of the present disclosure can include a plurality of charge sensors that are tethered to polymerases, the polymerases can be contacted with template nucleic acids and at least four different nucleotide types under conditions wherein the polymerases catalyze sequential addition of the nucleotide types to form nucleic acid complements of the nucleic acid templates; a series of changes in the signal from the polymerases can be detected using the charge sensors; and the sequences of nucleotides can be determined for the template nucleic acids. The plurality of polymerases present on the solid support can include at least two different types of polymerases. The different types of polymerases can optionally produce mutually distinguishable signals detectable by the charge sensors when incorporating the same type of nucleotide into a nascent nucleic acid strand. Distinguishing these mutually distinguishable signals can be used as a basis for determining the sequences for the plurality of nucleic acids.

Throughout this application various publications, patent applications or patents have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method for attaching a single polymerase to a single charge sensor, comprising:
    (a) providing a solid support comprising a plurality of charge sensors, wherein each of the charge sensors has a capacity to attach a plurality of polymerases;
    (b) providing a liquid comprising a plurality of polymerases, wherein each polymerase is bound to a nucleic acid repellant moiety and bound to a tether; and
    (c) contacting the solid support with the liquid under conditions wherein
        (i) the plurality of polymerases are in fluid communication with the plurality of charge sensors,
        (ii) a greater number of polymerases are in the fluid than the number of charge sensors on the solid support,
        (iii) polymerases from the liquid attach to the charge sensors via the tether, wherein a single polymerase attaches to a single charge sensor, and
        (iv) the nucleic acid repellant moiety bound to each of the polymerases prevents more than one of the polymerases from attaching to each of the charge sensors.

2. The method of claim 1, wherein the polymerases are DNA polymerases.

3. The method of claim 2 wherein the DNA polymerases are selected from the group consisting of DNA polymerases in Family A, DNA polymerases in Family B, DNA polymerases in Family C, DNA polymerases in Family D, DNA polymerases in Family X, DNA polymerases in Family Y, and DNA polymerases in Family RT.

4. The method of claim 1, wherein the tether has a nucleic acid sequence.

5. The method of claim 1, wherein the nucleic acid repellant moiety comprises a compacted nucleic acid with a ball or globular structure having an average diameter ranging from 0.1 µm to 5 µm.

6. The method of claim 1, wherein the polymerases comprise at least two different types of polymerases, wherein the different types of polymerases attach to individual charge sensors of the solid support.

7. The method of claim 6, wherein the different types of polymerases produce mutually distinguishable signals detectable by the charge sensors when incorporating the same type of nucleotide into a nascent nucleic acid strand.

8. The method of claim 1, wherein the nucleic acid repellant moiety occupies a volume of space that sterically hinders more than one of the polymerases from attaching to each of the charge sensors.

9. The method of claim 1, wherein the nucleic acid repellant moiety comprises a charge polarity that electrostatically hinders more than one of the polymerases from attaching to each of the charge sensors.

10. The method of claim 1, wherein each of the charge sensors has a capacity to attach more than two of the polymerases.

11. The method of claim 1, further comprising removing the bound nucleic acid repellant moiety from the polymerases after the polymerases attach to the charge sensors.

12. The method of claim 11, wherein the liquid is removed from the solid support before the removing of the bound nucleic acid repellant moiety and after the polymerases attach to the charge sensors.

13. The method of claim 1, wherein the tethers are conducting tethers selected from the group consisting of doped polythiophene, poly(3,4-ethylenedioxythiophene), polyacetylene, polypyrrole, polyaniline, polyfluorene, polyphenylene, polypyrene, polyazulene, polynaphthalenes, polycarbazole, polyindole, and polyazepine.

14. The method of claim 1, wherein the polymerase lacks a 3' to 5' exonuclease function.

15. The method of claim 14, wherein the polymerase comprises the large fragment of Bsu DNA polymerase I.

16. The method of claim 15, wherein the large fragment of Bsu DNA polymerase I is modified to include amino acid residues from the O-helix finger domain of Klenow fragment.

17. The method of claim 1, wherein the tether has a nucleic acid sequence of native ribonucleotides or analogs thereof.

18. The method of claim 1, wherein the tether has a nucleic acid sequence of native deoxyribonucleotides or analogs thereof.

19. The method of claim 1, wherein the charge sensor comprises a field-effect transistor (FET) selected from the group consisting of a silicon nanowire, a carbon nanotube, a single walled carbon nanotube, and a graphene nanoribbon.

20. The method of claim 1 wherein the polymerases are RNA polymerases selected from the group consisting of T7 RNA polymerase, RNA polymerase I, RNA polymerase II, RNA polymerase III, RNA polymerase IV, RNA polymerase V, and Archaea RNA polymerase.

21. The method of claim 3 wherein the DNA polymerases are the DNA polymerases in Family A and are selected from the group consisting of T7 DNA polymerase, eukaryotic mitochondrial DNA Polymerase γ, *E. coli* DNA Pol I, *Thermus aquaticus* Pol I, and *Bacillus stearothermophilus* Pol I.

22. The method of claim 3 wherein the DNA polymerases are the DNA polymerases in Family B and are selected from the group consisting of eukaryotic DNA polymerase α, eukaryotic DNA polymerase δ, eukaryotic DNA polymerase ε, T4 DNA polymerase, Phi29 DNA polymerase, and RB69 bacteriophage.

23. The method of claim 3 wherein the DNA polymerases are the DNA polymerases in Family C and includes *E. coli* DNA polymerase III alpha subunit.

24. The method of claim 3 wherein the DNA polymerases are the DNA polymerases in Family D and includes polymerases derived from Euryarchaeota subdomain of Archaea.

25. The method of claim 3 wherein the DNA polymerases are the DNA polymerases in Family X and are selected from the group consisting of eukaryotic polymerases Pol β, eukaryotic polymerases Pol σ, eukaryotic polymerases Pol λ, eukaryotic polymerases Pol µ, and *S. cerevisiae* Pol4.

26. The method of claim 3 wherein the DNA polymerases are the DNA polymerases in Family Y and are selected from the group consisting of Pol η, Pol iota, Pol kappa, *E. coli* Pol IV, and *E. coli* Pol V.

27. The method of claim 3 wherein the DNA polymerases are the DNA polymerases in Family RT and are selected from the group consisting of retrovirus reverse transcriptases and eukaryotic telomerases.

28. A method for attaching a single polymerase to a single charge sensor, comprising:
  (a) providing a solid support comprising a plurality of charge sensors, wherein each of the charge sensors has a capacity to attach a plurality of polymerases;
  (b) providing a liquid comprising a plurality of polymerases, wherein each polymerase is bound to a tether; and
  (c) contacting the solid support with the liquid; and
  (d) applying an electric field, wherein
    the plurality of polymerases are in fluid communication with the plurality of charge sensors,
    a greater number of polymerases are in the fluid than the number of charge sensors on the solid support,
    polymerases from the fluid attach to the charge sensors via the tether, wherein a single polymerase attaches to a single charge sensor, and
    the electric field actively transports the polymerases to the charge sensors.

* * * * *

UNITED STATES PATENT AND TRADEMARK OFFICE
CERTIFICATE OF CORRECTION

PATENT NO. : 10,545,115 B2  
APPLICATION NO. : 15/839795  
DATED : January 28, 2020  
INVENTOR(S) : Boyan Boyanov et al.

Page 1 of 1

It is certified that error appears in the above-identified patent and that said Letters Patent is hereby corrected as shown below:

In the Specification

In Column 1, Line 5, after "which" insert -- is --, therefor.

In the Claims

In Column 42, Line 30, in Claim 25, delete "Pol4." and insert -- Pol IV. --, therefor.

Signed and Sealed this  
Twelfth Day of May, 2020

Andrei Iancu  
*Director of the United States Patent and Trademark Office*